United States Patent
Yamashita

(10) Patent No.: US 10,022,047 B2
(45) Date of Patent: Jul. 17, 2018

(54) OPHTHALMIC APPARATUS

(71) Applicant: CANON KABUSHIKI KAISHA, Tokyo (JP)

(72) Inventor: Yutaka Yamashita, Shiroi (JP)

(73) Assignee: Canon Kabushiki Kaisha, Tokyo (JP)

( * ) Notice: Subject to any disclaimer, the term of this patent is extended or adjusted under 35 U.S.C. 154(b) by 15 days.

(21) Appl. No.: 15/253,260

(22) Filed: Aug. 31, 2016

(65) Prior Publication Data

US 2017/0065170 A1   Mar. 9, 2017

(30) Foreign Application Priority Data

Sep. 4, 2015  (JP) ................... 2015-175023

(51) Int. Cl.
- *A61B 3/10* (2006.01)
- *A61B 3/00* (2006.01)
- *A61B 3/14* (2006.01)

(52) U.S. Cl.
CPC ............ *A61B 3/102* (2013.01); *A61B 3/0025* (2013.01); *A61B 3/0058* (2013.01); *A61B 3/10* (2013.01); *A61B 3/14* (2013.01)

(58) Field of Classification Search
CPC ..... A61B 3/102; A61B 3/0025; A61B 3/0058; A61B 3/14; A61B 3/10
USPC ....................................................... 351/206
See application file for complete search history.

(56) References Cited

U.S. PATENT DOCUMENTS

| | | | | |
|---|---|---|---|---|
| 8,169,618 | B2* | 5/2012 | Inoue ................. | A61B 1/00096 356/479 |
| 9,014,451 | B2* | 4/2015 | Beg .................... | G01N 21/4795 356/479 |
| 9,023,016 | B2* | 5/2015 | Goldshleger ....... | A61F 9/00825 606/2 |
| 9,066,784 | B2* | 6/2015 | Goldshleger ....... | A61F 9/00825 |
| 9,585,560 | B2* | 3/2017 | Iwase .................. | A61B 3/0025 |
| 2009/0279098 | A1* | 11/2009 | Ohbayashi .......... | A61B 5/0066 356/478 |
| 2011/0141259 | A1* | 6/2011 | Nakano ............... | A61B 3/0025 348/78 |
| 2013/0004046 | A1* | 1/2013 | Nakano ................ | A61B 3/102 382/131 |
| 2013/0195340 | A1* | 8/2013 | Iwase ................. | G06K 9/00617 382/131 |
| 2014/0085606 | A1* | 3/2014 | Miyasa ................ | G06T 7/0012 351/206 |
| 2014/0205169 | A1* | 7/2014 | Yamakawa .......... | G06T 7/0012 382/131 |
| 2015/0230701 | A1* | 8/2015 | Sato ..................... | A61B 3/102 351/206 |

(Continued)

FOREIGN PATENT DOCUMENTS

JP          2014-014727 A          1/2014

*Primary Examiner* — William R Alexander
(74) *Attorney, Agent, or Firm* — Canon USA Inc., IP Division

(57) ABSTRACT

An ophthalmic apparatus includes a deforming unit and a generation unit. The deforming unit deforms a shape of a boundary that defines a region of a tomographic image of a subject eye in a depth direction according to a thickness of a layer in which the boundary is positioned. The generation unit generates an en-face image based on the region in the depth direction defined by the shape of the boundary deformed by the deforming unit.

14 Claims, 19 Drawing Sheets

(56) References Cited

U.S. PATENT DOCUMENTS

| | | | |
|---|---|---|---|
| 2015/0294468 A1* | 10/2015 | Shimizu | G01B 9/02091 |
| | | | 356/479 |
| 2015/0366452 A1* | 12/2015 | Iwase | A61B 3/0025 |
| | | | 351/206 |
| 2015/0374227 A1* | 12/2015 | Takeno | A61B 3/102 |
| | | | 600/425 |
| 2016/0358347 A1* | 12/2016 | Uchida | A61B 3/102 |
| 2017/0014025 A1* | 1/2017 | Uchida | A61B 3/0025 |
| 2017/0035291 A1* | 2/2017 | Jiao | A61B 3/102 |

\* cited by examiner

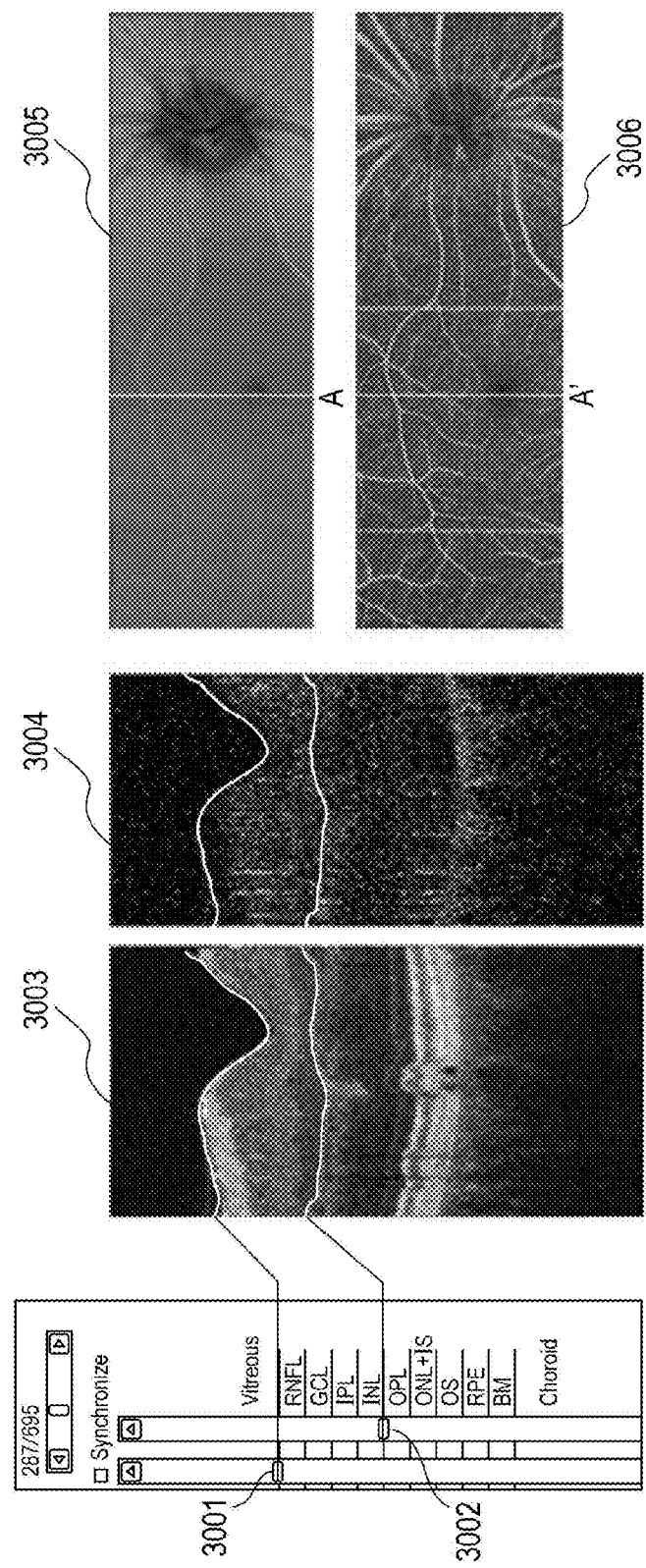

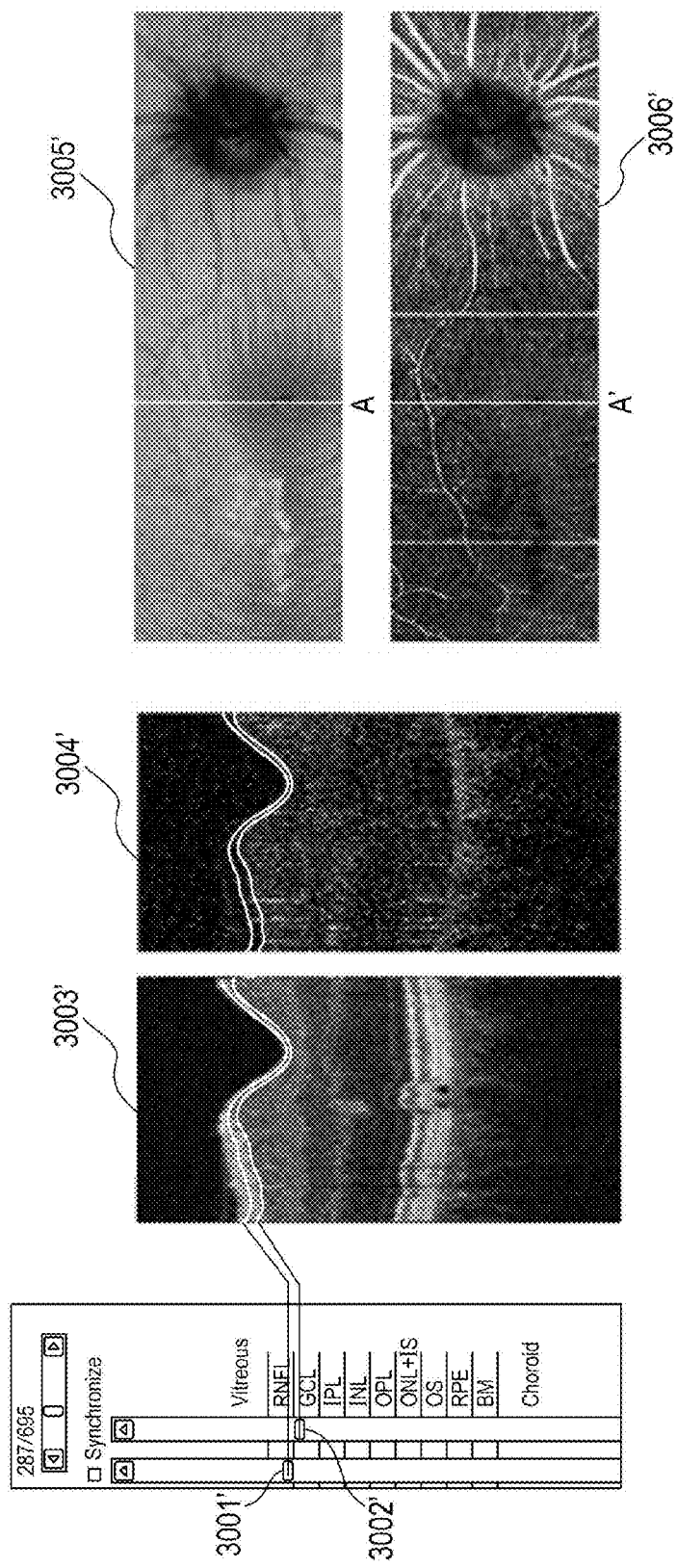

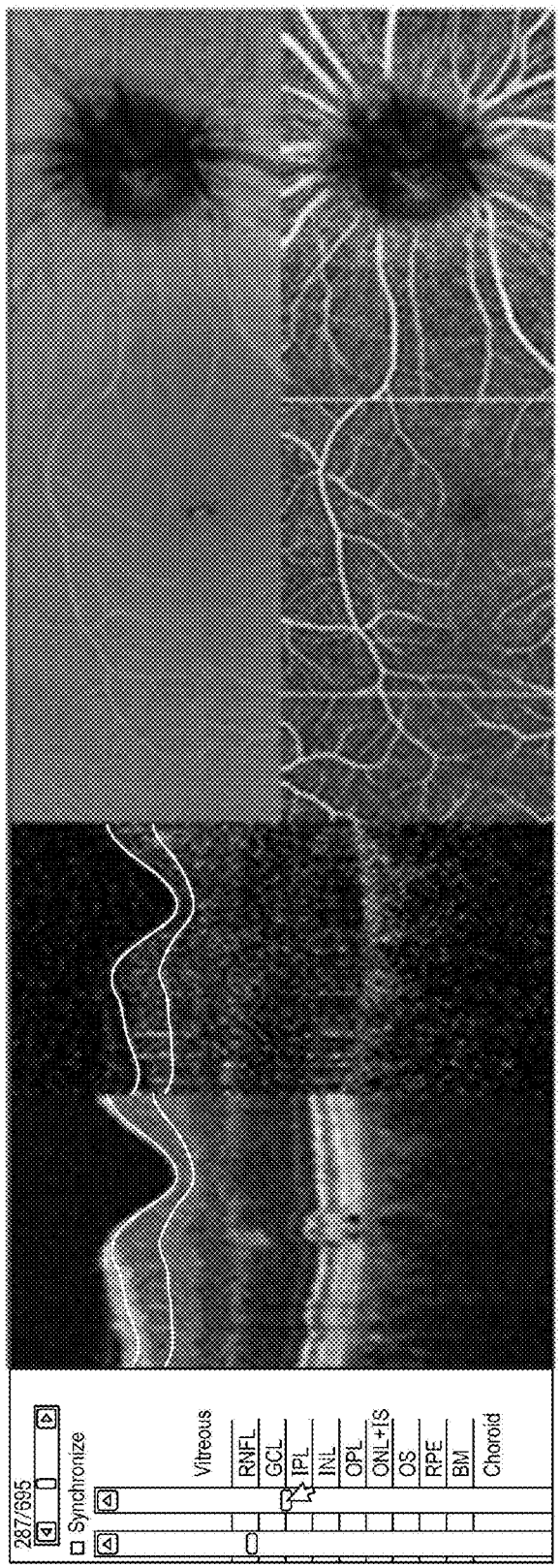

OPHTHALMIC APPARATUS

BACKGROUND OF THE INVENTION

Field of the Invention

The disclosure of the present application relates to an ophthalmic apparatus.

Description of Related Art

Optical coherence tomography (OCT) is in practical use as a method for nondestructively and noninvasively acquiring tomographic images of a measurement object, such as a living organism. The OCT is widely used particularly to acquire tomographic images of a retina on the eye fundus of a subject eye for the ophthalmic diagnosis of the retina in the field of ophthalmology.

Japanese Patent Application Laid-Open No. 2014-014727 discloses a technique for generating an integrated image by adding images of any layers of tomographic images acquired by OCT and by averaging them.

SUMMARY OF THE INVENTION

An aspect of the present disclosure describes an ophthalmic apparatus including a deforming unit configured to deform a shape of a boundary that defines a region of a tomographic image of a subject eye in a depth direction according to a thickness of a layer in which the boundary is positioned, and a generation unit configured to generate an en-face image based on the region in the depth direction defined by the shape of the boundary deformed by the deforming unit.

Further features of the present invention will become apparent from the following description of exemplary embodiments with reference to the attached drawings.

BRIEF DESCRIPTION OF THE DRAWINGS

FIG. 9A is a diagram illustrating an example of a GUI according to an embodiment.

FIG. 9B is a diagram illustrating an example of a GUI according to an embodiment.

FIG. 10A is a diagram illustrating an example of a GUI according to an embodiment.

DESCRIPTION OF THE EMBODIMENTS

Image capturing apparatuses according to embodiments of the present disclosure will be described hereinbelow with reference to the accompanying drawings. The configurations shown in the following embodiments are mere examples and are not intended to limit the present disclosure. Although the subject in the embodiments is a human eye (an eye fundus), the subject can be skin or another organism. Although the object to be imaged is the eye fundus of the eye, the anterior segment of the eye can also be imaged.

First Embodiment

Configuration of Overall Image Forming Apparatus

Figure 1:
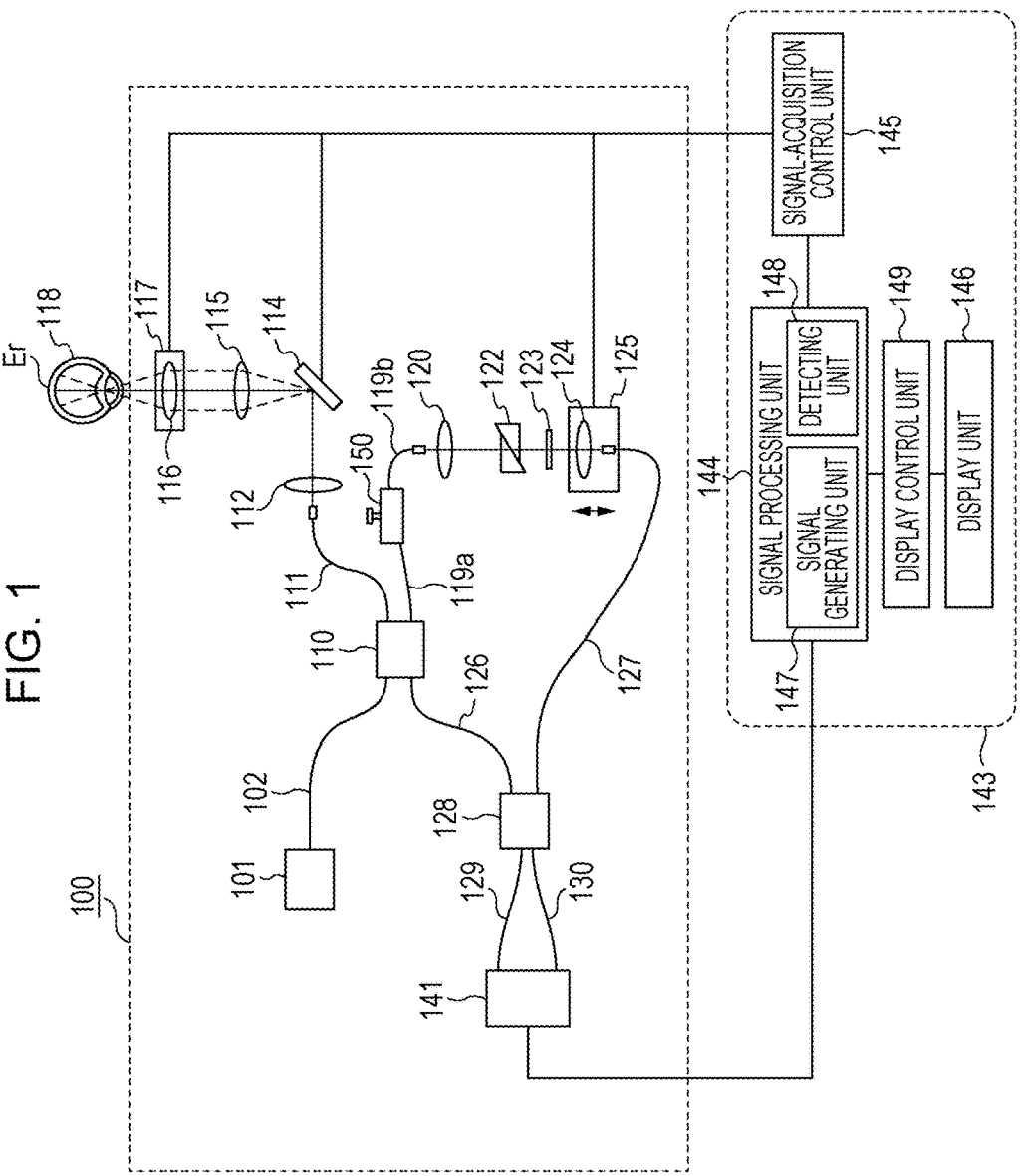
FIG. 1 is a diagram illustrating, in outline, an example of the overall configuration of an image forming apparatus according to an embodiment of the present disclosure.

FIG. 1 is a diagram illustrating a configuration example of an image forming apparatus (an ophthalmic apparatus) using optical coherence tomography according to a first embodiment. The apparatus shown in FIG. 1 includes an optical-coherence-tomographic-image acquiring unit 100 that acquires optical coherence tomographic signals and a control unit 143. The control unit 143 includes a signal processing unit 144, a signal-acquisition control unit 145, a display unit 146, and a display control unit 149. The signal processing unit 144 includes an image generating unit 147 and a detecting unit 148. One example of the control unit 143 is a computer. A CPU disposed in the computer executes programs stored in a storage unit (not shown) to cause the control unit 143 to function as the signal processing unit 144, the signal-acquisition control unit 145, the image generating unit 147, the detecting unit 148, and the display control unit 149.

The control unit 143 may include one or more CPUs and storage units. In other words, a least one processing unit (CPU) and at least one storage unit (RAM or ROM) are connected to each other. When at least one processing unit executes the programs stored in at least one storage unit, the control unit 143 functions as the above units. The processing unit is not limited to the CPU. In some embodiments, the processing unit is a field-programmable gate array (FPGA) circuit or card.

First, the configuration of the optical-coherence-tomographic-image acquiring unit 100 will be described. FIG. 1 is a diagram illustrating a configuration example of an OCT apparatus as an example of the optical-coherence-tomographic-image acquiring unit according to the first embodiment. Examples of the OCT apparatus include a spectral-domain (SD)-OCT and a swept-source (SS)-OCT. This embodiment shows a configuration in the case where the OCT apparatus is an SS-OCT.

Configuration of OCT Apparatus 100

The configuration of the OCT apparatus 100 will be described.

A light source 101 is a swept source (hereinafter abbreviated as SS) light source, which emits light while sweeping the wavelength with a central wavelength of 1,050 nm and a sweeping width of 100 nm. The wavelength and the sweeping width are mere examples and are not intended to limit the present disclosure. The numerical values in the following embodiments are mere examples and are not intended to limit the present disclosure.

The light emitted from the light source 101 is guided to a beam splitter 110 through an optical fiber 102, where it is split into measurement light (also referred to as OCT measurement light) and reference light (also referred to as reference light corresponding to the OCT measurement light. The split ratio of the beam splitter 110 is, for example, 90 (reference light): 10 (measurement light). The split measurement light is discharged through an optical fiber 111 and is collimated by a collimator 112. The collimated measurement light passes a galvanometer scanner 114 that scans the measurement light at the eye fundus Er of a subject eye 118, a scanning lens 115, and a focus lens 116 and enters the subject eye 118. Although the galvanometer scanner 114 is illustrated as a single mirror, the actual galvanometer scanner 114 includes two galvanometer scanners: an X-axis scanner 114a and a Y-axis scanner 114b (not shown) so as to raster-scan the eye fundus Er of the subject eye 118. The focus lens 116 is secured on a stage 117 and can adjust the focus by moving in an optical axis direction. The galvanometer scanner 114 and the stage 117 are controlled by the signal-acquisition control unit 145 and is capable of scanning the measurement light across a desired range of the eye fundus Er of the subject eye 118 (also referred to as a tomographic-image acquisition range, a tomographic-image acquisition position, or a measurement-light irradiation position).

The OCT apparatus 100 may have a tracking function for detecting the motion of the eye fundus Er and moving the mirror of the galvanometer scanner 114 along with the motion of the eye fundus Er, although not described in detail in this embodiment. The tracking can be performed using a general technique and in real time or by post-processing. One example is a method using a scanning laser ophthalmoscope (SLO). This is a method for acquiring time-series two-dimensional images (eye fundus surface images) of the eye fundus Er in a plane perpendicular to the optical axis and extracting feature portions of the images, such as vascular bifurcations, using the SLO. This allows real-time tracking by calculating the movement of the feature portions of the acquired two-dimensional images as the amount of movement of the eye fundus Er and by feeding back the calculated amount to the galvanometer scanner 114.

The measurement light enters the subject eye 118 and is focused on the eye fundus Er by the focus lens 116 on the stage 117. The measurement light that irradiates the eye fundus Er is reflected and scattered from the individual retina layers back to the beam splitter 110 through the above-described optical path. The measurement light that has returned to the beam splitter 110 enters a beam splitter 128 through an optical fiber 126.

The reference light split by the beam splitter 110 exits through an optical fiber 119a, a polarization control unit 150, and an optical fiber 119b and is collimated by a collimator 120. The polarization control unit 150 is capable of changing the polarization of the reference light to desired polarization. The reference light passes through a dispersion compensating glass 122, a neutral density (ND) filter 123, and a collimator 124 into an optical fiber 127. The collimator 124 and one end of the optical fiber 127 are secured on a coherent gate stage 125 and are controlled by the signal-acquisition control unit 145 so as to be driven in the optical axis direction according to the axial length of the eyeball of the subject. In this embodiment, the optical path length of the reference light is changed. Alternatively, the optical path length of the measurement light may be changed because it is only required that the difference between the optical path length of the measurement light and the optical path length of the reference light can be changed.

The reference light that has passed through the optical fiber 127 enters the beam splitter 128. The beam splitter 128 couples the return light of the reference light and the reference light together into interfering light and then splits the interfering light into two. The interfering light is split into interfering lights with opposite phases (hereinafter expressed as a positive component and a negative component). The positive component of the split interfering light passes through an optical fiber 129 into one of input ports of a detector 141. In contrast, the negative component of the interfering light passes through an optical fiber 130 into the other port of the detector 141. The detector 141 is a differential detector. Upon receiving two interfering lights with 180-degree opposite phases, the detector 141 removes a direct-current component and outputs interfering signals including only an interfering component.

The interfering light detected by the detector 141 is output as electrical signals (interfering signals) according to the intensity of the light and is input to the signal processing unit 144, which is an example of a tomographic-image generating unit.

Control Unit 143

The control unit 143 for controlling the entire OCT apparatus 100 will be described.

The control unit 143 includes the signal processing unit 144, the signal-acquisition control unit 145, the display unit 146, and the display control unit 149. The signal processing unit 144 includes the image generating unit 147 and the detecting unit 148. The image generating unit 147 has a function for generating a luminance image and a motion contrast image (an image showing blood flow portions or an image showing blood vessels) from electrical signals (interfering signals) sent from the detector 141. The detecting unit 148 has a function for generating layer information (segmentation of the retina) by detecting the layer boundaries of the retina from the luminance image.

The signal-acquisition control unit 145 controls individual components as described above. The signal processing unit 144 generates images, analyzes the generated images, and generates visual information on the analytical result on the basis of the interfering signals output from the detector 141.

The images and the analytical result generated by the signal processing unit 144 are sent to the display control unit 149. The display control unit 149 causes the images and the analytical result to be displayed on the display screen of the display unit 146. One example of the display unit 146 is a liquid-crystal display. After the image data generated by the signal processing unit 144 is sent to the display control unit 149, the image data may be transmitted to the display unit 146 either by wire or by radio. Although the display unit 146 and so on of this embodiment are included in the control unit 143, they may be disposed separately from the control unit 143, for example, in a tablet, which is one example of user-potable devices. In this case, the display unit may have a touch panel function to allow movement of an image display position, scaling, and change of the display image, and so on.

This is the process of acquiring information on tomographic images of one point of the subject eye 118. The acquisition of information on tomographic images of the subject eye 118 in the depth direction is referred to as A-scan. Scanning for acquiring information on the cross-section of the subject eye 118 in a direction perpendicular to A-scan, that is, a two-dimensional image, is referred to as B-scan, and scanning in a direction perpendicular to the tomographic image acquired by B-scan is referred to as C-scan. In other words, in two-dimensional raster scanning of an eye fundus for acquiring a three-dimensional tomographic image, high-speed scanning is referred to as B-scan, and low-speed scanning perpendicular to the B-scan is referred to as C-scan. Performing the A-scan and the B-scan allows a two-dimensional tomographic image to be acquired, and performing the A-scan, the B-scan, and the C-scan allows a three-dimensional tomographic image to be acquired. The B-scan and the C-scan are performed by the galvanometer scanner 114 described above.

The X-axis scanner 114a and the Y-axis scanner 114b (not shown) are deflecting mirrors whose rotation axes intersect each other at right angles. The X-axis scanner 114a is used for scanning in the X-axis direction, and the Y-axis scanner 114b is used for scanning in the Y-axis direction. The X-axis direction and the Y-axis direction are perpendicular to the axis of the eyeball and perpendicular to each other. The line scanning directions of the B-scan and the C-scan may not align with the X-axis direction or the Y-axis direction. This allows the line scanning directions of the B-scan and the C-scan to be determined according to whether a two-dimensional tomographic image or three-dimensional tomographic image is to be captured.

Scan Pattern

Figure 2:
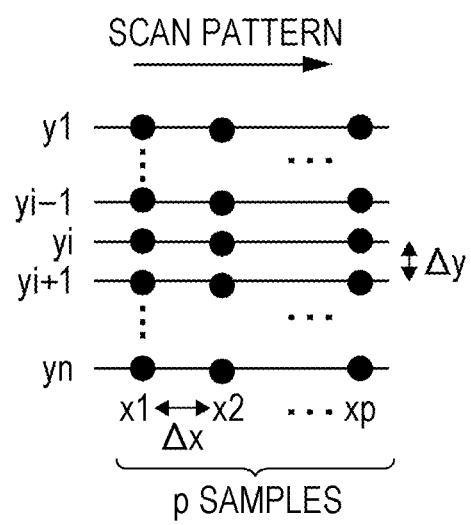
FIG. 2 is a diagram illustrating an example of a scan pattern according to an embodiment.

Referring next to FIG. 2, an example of scan patterns of this embodiment will be described.

OCT angiography requires a plurality of measuring operations at the same position (or substantially the same position) to measure temporal changes of OCT interfering signals due to blood flow. In this embodiment, the OCT apparatus 100 moves to n y-positions while repeating the B-scan m times at the same position.

A specific scan pattern is illustrated in FIG. 2. The B-scan is repeated m times on n y-positions from y1 to yn on an eye fundus surface.

The greater the value m, the larger the number of measuring operations at the same position, increasing the blood flow detection accuracy. However, this increases the scanning time, which in turn causes the generating of a motion artifact in the image because of the motion of the eye (involuntary eye motion) and the increasing of discomfort on the subject. In this embodiment, therefore, the scanning is performed at m=4 in view of the balance between advantages and the disadvantages. The control unit 143 may change the value of m according to the A-scan speed of the OCT apparatus 110, and the analytical result of the motion on the eye fundus surface image of the subject eye 118. In other words, the value of m is not limited to 4. In some embodiments, m is another value.

In FIG. 2, p denotes the sampling frequency of the A-scan during one B-scan. In other words, the size of the planar image is determined by p×n. The greater p×n, the larger the area can be scanned at the same measuring pitch, but this increases the scanning time, which results in the above-described creation of motion artifacts and a discomfort to the patient. In this embodiment, the scanning is performed at n=p=300 in view of establishing a balance between the advantages and the disadvantages. Note that n and p can be freely changed.

In FIG. 2, $\Delta x$ is the interval (x-pitch) between adjacent x-positions, and $\Delta y$ is the interval (y-pitch) between adjacent y-positions. In this embodiment, the x-pitch and the y-pitch are set to one half of the spot diameter of the irradiation light on the eye fundus Er; that is, the x-pitch and the y-pitch are set to 10 μm. Setting the x-pitch and the y-pitch to one half of the diameter of the beam spot on the eye fundus Er allows a high-definition image to be formed. Even if the x-pitch and the y-pitch are set smaller than one half of the beam spot diameter on the eye fundus Er, the effect of increasing the definition of the image is small.

In contrast, setting the x-pitch and the y-pitch to a value larger than one half of the diameter of the beam spot on the eye fundus Er will decrease the definition but allows an image of a wider region to be captured with a requirement for smaller data capacity. The x-pitch and the y-pitch may be freely changed according to a clinical request.

The scanning area of this embodiment is p×$\Delta x$=3 mm in the x-direction, and n×$\Delta y$=3 mm in the y-direction. The values of the scanning area are not limited to above values.

Figure 3:
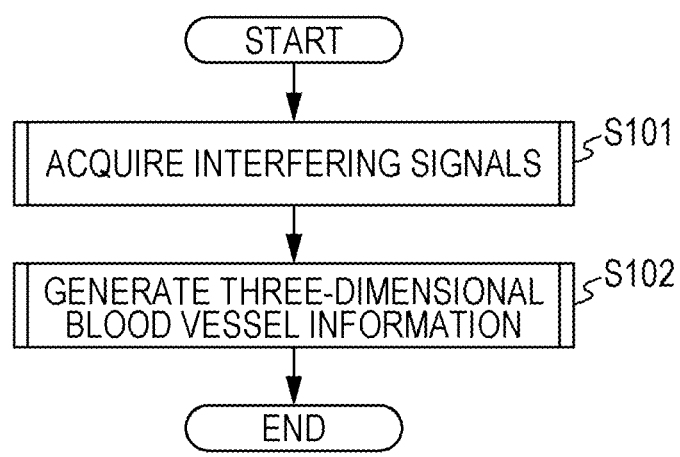
FIG. 3 is a diagram illustrating an example of an overall processing sequence according to an embodiment.

Referring next to FIG. 3, an example of a processing sequence of a method for forming images according to this embodiment will be described. At step S101, the signal-acquisition control unit 145 controls the optical-coherence-tomographic-image acquiring unit 100 to acquire optical coherence tomographic signals. The details of this process will be described later. At step S102, the control unit 143 generates display information. The details of the process of S102 will also be described later. Thus, the processing sequence of the method for forming images according to this embodiment ends.

Procedure for Acquiring Interfering Signals

Figure 4:
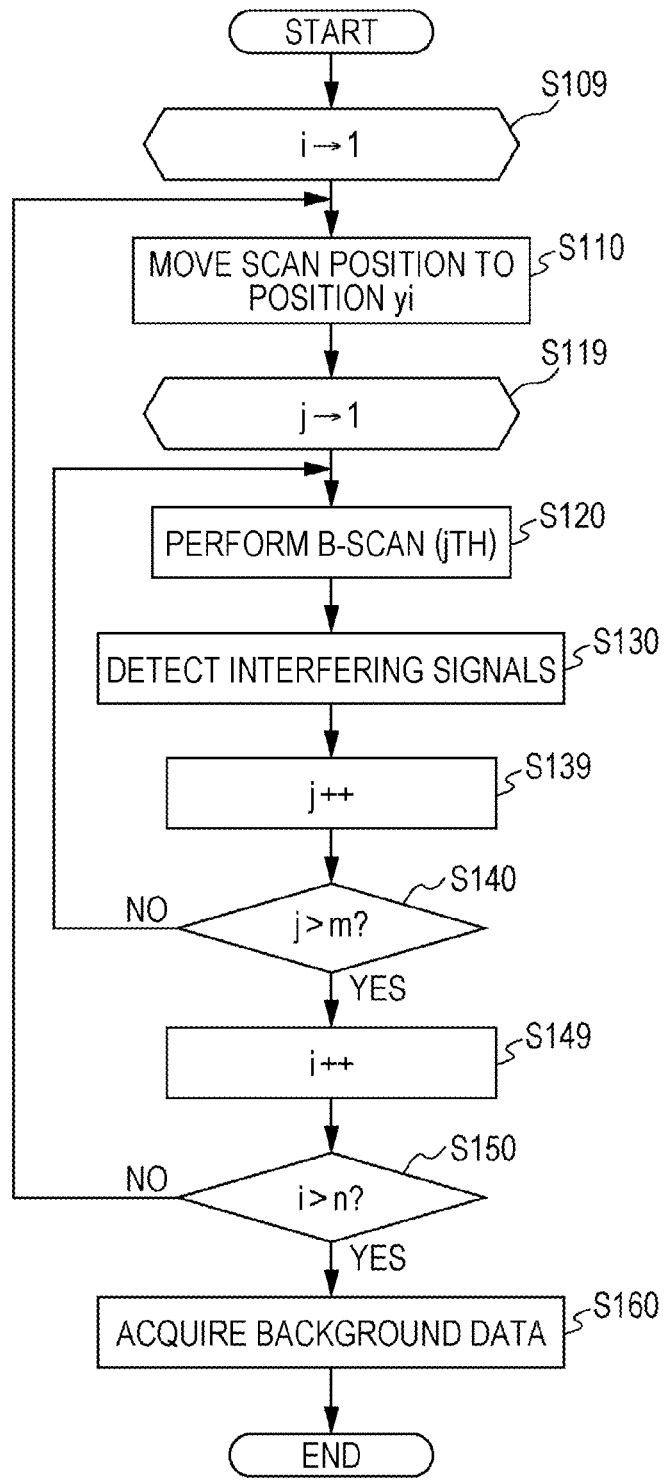
FIG. 4 is a diagram illustrating an example of a procedure for acquiring interfering signals according to an embodiment.

Referring to FIG. 4, an example of a specific procedure for acquiring interfering signals at step S101 of this embodiment will be described. In FIG. 4, at step S109, the signal-acquisition control unit 145 sets the index i of the position yi to 1. At step S110, the OCT apparatus 100 moves the scanning beam to position yi. At step S119, the signal-acquisition control unit 145 sets the index j of repeated B-scans to 1. At step S120, the OCT apparatus performs the B-scans.

At step S130, the detector 141 detects an interfering signal in each A-scan. The interfering signals are stored in a non-illustrated memory of the signal processing unit 144 via an analog-to-digital converter (not shown). The signal processing unit 144 acquires p samples of the interfering signals of the A-scan as interfering signals of one B-scan.

At step S139, the signal-acquisition control unit 145 increments the index j of the repeated B-scans.

At step S140, the signal-acquisition control unit 145 determines whether j is larger than a predetermined number (m). In other words, the signal-acquisition control unit 145 determines whether the B-scan at position yi has been repeated m times. If NO, the process returns to S120 and repeats the B-scan measurement at the same position. If YES, the process advances to S149. At step S149, the signal-acquisition control unit 145 increments the index i of position yi. At step S150, the signal-acquisition control unit 145 determines whether i is larger than a predetermined number of measuring operations (n) at y-positions. In other word, the control unit 145 determines whether the B-scans are performed at all n y-positions. If "i" is less than the predetermined number of measuring operations (n) at y-positions (NO in S150), the process returns to S110, and measurement at the next "i" position is performed. If the predetermined number of measuring operations (n) at the y-positions end (YES at S150), the process goes to the next step S160. Thus, the signal processing unit 144 can acquire three-dimensional tomographic image data by performing the above steps.

At step S160, the OCT apparatus 100 acquires background data. The OCT apparatus 100 performs 100 A-scans, with a shutter closed. The signal-acquisition control unit 145 averages the 100 A-scans and stores the averaged value. The number of times of measuring the background is not limited to 100.

Thus, the interfering signal acquisition process of this embodiment ends.

Procedure for Signal Processing

Figure 5:
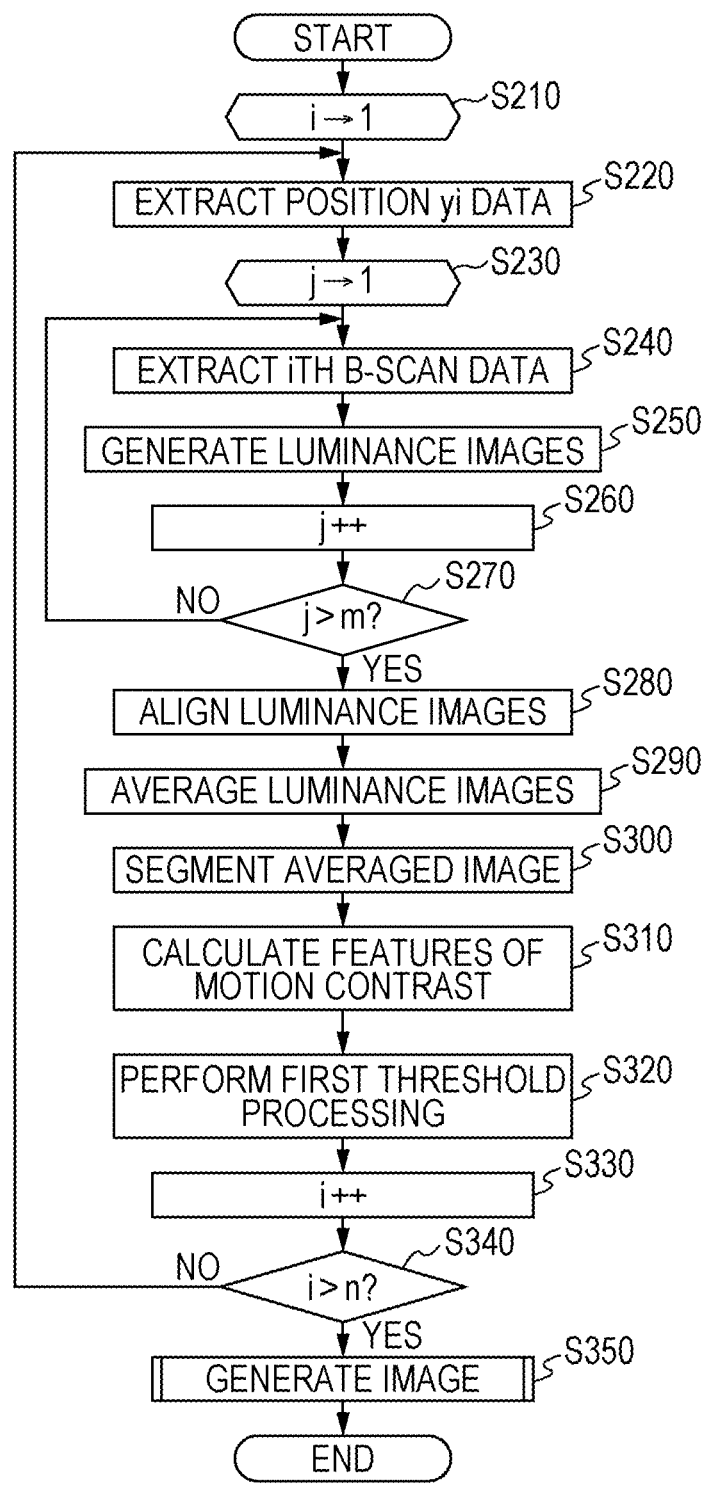
FIG. 5 is a diagram illustrating an example of a procedure for signal processing according to an embodiment.

Referring next to FIG. 5, an example of a specific procedure for generating information on a three-dimensional blood flow region at step S102 of this embodiment will be described.

This embodiment needs to calculate motion contrast to generate three-dimensional blood flow region information.

Here, a feature for distinguishing between flowing tissue (for example, blood) and nonflowing tissue of the subject tissue is simply defined as motion contrast (or a motion contrast feature or a motion contrast value). A method for calculating the motion contrast will be described later.

In FIG. 5, at step S210, the image generating unit 147 sets the index i of the position yi to 1. At step S220, the signal processing unit 144 extracts interfering signals (m) of repeated B-scans at position yi from the interfering signals acquired in the process shown in FIG. 4. At step S230, the image generating unit 147 sets the index j of the repeated B-scans to 1. At step S240, the signal processing unit 144 extracts the interfering signal of the jth B-scan.

At step S250, the image generating unit 147 generates a luminance tomographic image by performing a general reconstructing process on the B-scan interfering signal extracted at step S240. Specifically, the image generating unit 147 first removes fixed-pattern noise formed of background data from the interfering signal. The fixed-pattern noise is extracted by averaging a detected plurality of A-scan signals on background data and then subtracting the fixed-pattern noise from the interfering signal. Next, the image generating unit 147 performs desired window function processing to optimize the depth resolution and dynamic range, which have a trade-off relationship when Fourier-transformed in a finite interval. The image generating unit 147 performs a fast Fourier transform (FFT) to generate a luminance tomographic image. By performing the process at step S250 on the three-dimensional tomographic image data acquired at the process in FIG. 4, a three-dimensional tomographic image is acquired.

At step S260, the image generating unit 147 increments the index j. At step S270, the image generating unit 147 determines whether the index j is larger than m. In other words, the image generating unit 147 determines whether the generation of a luminance image by B-scan at position yi is repeated m times. If the determination at step S270 is No, the process returns to step S240, and the image generating unit 147 repeats the generation of a luminance image by B-scan at the same Y-position. In other words, the image generating unit 147 acquires a plurality of tomographic images of substantially the same portion of the subject eye Er.

If it is determined to be Yes at step S270, the process goes to step S280. At step S280, the image generating unit 147 aligns the luminance images of m frames by the repeated B-scans at position yi. Specifically, the image generating unit 147 first selects any one tomographic image as a template from the m frames. The frame to be selected as a template may be selected in such a manner that the correlation is calculated for all combinations, the sum of coefficients of correlation is obtained for each frame, and a frame in which the sum is the maximum is selected as a template. Next, the image generating unit 147 compares the individual frames with the template to obtain the amount of the positional misalignment ($\delta X$, $\delta Y$, $\delta \theta$). Specifically, the image generating unit 147 calculates normalized cross-correlation (NCC), which is an index indicating the similarity, while changing the position and angle of the template images and determines the difference between the image positions when the value is the maximum as the amount of positional misalignment.

In some embodiments, the index indicating the similarity can be any index indicating the similarity between the template and the features of the images in the frames. For example, the sum of absolute difference (SAD), the sum of squared difference (SSD), or zero-means normalized cross-correlation (ZNCC) can be used. Other examples are phase only correlation (POC) and rotation invariant phase only correlation (RIPOC).

Next, the image generating unit 147 applies position correction to m−1 frames other than the template according to the amount of positional misalignment ($\delta X$, $\delta Y$, $\delta \theta$) to align the m frames.

At step S290, the image generating unit 147 averages the luminance images aligned at step S280 to generate an averaged-luminance image.

At step S300, the detecting unit 148 performs segmentation of the retina (acquisition of regional information) on the averaged-luminance image generated by the image generating unit 147 at step S290. For example, the detecting unit 148 detects a plurality of layer boundaries of the retina from the averaged-luminance image and generates data indicating the coordinates of the layer boundaries. The detecting unit 148 may detect a plurality of layer boundaries from a luminance image before being averaged.

At step S310, the image generating unit 147 calculates motion contrast. In this embodiment, the image generating unit 147 calculates the variances of the signal intensity (luminance), as the motion contrast, for each pixel at the same position from the luminance tomographic images of m frames output from the image generating unit 147 at step S300. In other words, the image generating unit 147 calculates the motion contrast using corresponding pixel data of the calculated plurality of tomographic image data pieces. In addition to the variances, any of a standard deviation, a difference value, a decorrelation value, and a correlation value may be used. Not the signal intensity but the phase may be used.

The motion contrast can be obtained in various ways. In some embodiments, the feature of the motion contrast is any index that indicates a change in luminance of the pixels of a plurality of B-scan images at the same Y-position.

At step S320, the image generating unit 147 performs first threshold processing on the motion contrast. The value for the first threshold processing can be set to (the average luminance of a noise floor+2σ) by extracting an area in which only random noise is displayed in the noise floor from the averaged-luminance image that the image generating unit 147 outputs at step S311 and calculating a standard deviation σ. The image generating unit 147 sets the value of motion contrast in which the luminance is equal to less than the threshold to, for example, 0.

Thus, the noise can be reduced by removing motion contrast caused by changes in luminance due to random noise by the first threshold processing at step S320.

The smaller the value for the first threshold processing, the higher the sensitivity for detecting motion contrast, but the more the noise component. The larger the value, the less the noise but the lower the sensitivity for detecting motion contrast.

In this embodiment, the threshold is set to (the average luminance of a noise floor+2σ), but the threshold is not limited to the above value.

At step S330, the image generating unit 147 increments the index i of position yi.

At step S340, the image generating unit 147 determined whether i is greater than n. In other words, the image generating unit 147 determines whether alignment at n y-positions, averaging of luminance images, calculation of motion contrast, and threshold processing have been completed. If No at step S340, the process returns to step S220. If yes, the process goes to step S350.

At the point where step S340 ends, the averaged-luminance images of the pixels of B-scan images and motion-contrast three-dimensional data at all Y-positions (Z [depth]- and X-direction data) have been acquired. The B-scan images at the plurality of Y-positions correspond to a three-dimensional tomographic image.

At step S350, the image generating unit 147 generates a three-dimensional motion contrast image using the three-dimensional motion contrast data. The image generating unit 147 can also generate a two-dimensional motion contrast image (a motion-contrast en-face image) in which motion contrast is projected or integrated in any depth range of the retina in the three-dimensional motion contrast image. In other words, the image generating unit 147 integrates motion contrast in a predetermined range in the depth direction of the subject eye 118 to generate the en-face image. Any depth range of the retina may be selected using the information on the layer boundaries acquired at step S300. As used herein, "en-face" refers to an imaging technique derived from spectral domain optical coherence tomography (OCT). It produces frontal sections of retinal layers, also referred to as "C-scan OCT." En-face OCT has the potential to enable high-resolution analysis and quantification of pathological structures such as reticular pseudodrusen (RPD) and choroidal neovascularization, which can be used as markers for disease monitoring of a subject's eye.

The image generating unit 147 may generate the en-face image by extracting the representative value of motion contrast in a predetermined range in the depth direction of the subject eye 118, such as a mean value, a median value, or a maximum value, and by projecting the representative value in the depth direction.

Since the tomographic image used to acquire the motion contrast and the tomographic image subjected to the segmentation are the same tomographic image, the result of segmentation can be associated with the three-dimensional motion contrast image. Even if the tomographic image used to acquire the motion contrast and the tomographic image subjected to the segmentation are not the same tomographic image, the result of segmentation can be associated with the three-dimensional motion contrast image. For example, by aligning the tomographic image used to acquire the motion contrast and the tomographic image subjected to the segmentation, the result of segmentation can be associated with the three-dimensional motion contrast image.

The image generating unit 147 can also generate a two-dimensional luminance image (a luminance en-face image) in which luminance is projected or integrated in any depth range of the retina in the three-dimensional tomographic image acquired in the above process. Any depth range of the retina may be selected using the information on the layer boundaries acquired at step S300. The image generating unit 147 may generate the en-face image using the representative value of luminance in a predetermined range in the depth direction of the subject eye 118, such as a mean value, a median value, or a maximum value.

The en-face image may be generated using known various techniques.

Figure 6:
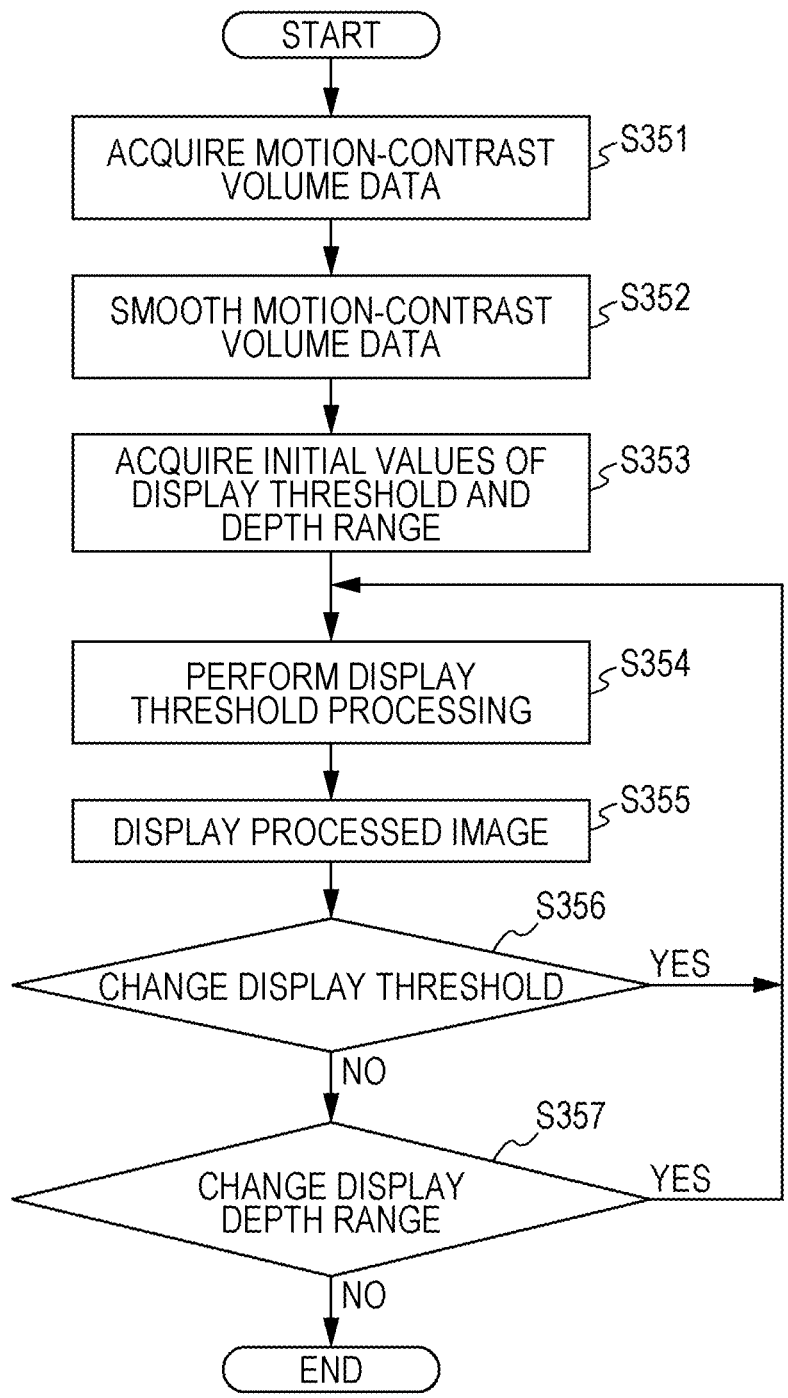
FIG. 6 is a diagram illustrating an example of a procedure for acquiring three-dimensional region information according to an embodiment.

FIG. 6 shows the details of step S350.

At step S351, the image generating unit 147 acquires three-dimensional data on the motion contrast acquired by the processes at step S310 and 320.

At step S352, the image generating unit 147 performs a smoothing process on the motion-contrast three-dimensional data to remove noise, with blood flow information left.

Examples of the smoothing process are as follows, although it depends on the characteristics of motion contrast: a smoothing method of outputting the maximum value of the motion contrast of nx×ny×nz voxels in the vicinity of a target pixel; a smoothing method of outputting the mean value of the motion contrast of nx×ny×nz voxels in the vicinity of a target pixel; a smoothing method of outputting the median value of the motion contrast of nx×ny×nz voxels in the vicinity of a target pixel; a smoothing method of assigning weights of distance to the motion contrast of nx×ny×nz voxels in the vicinity of a target pixel; a smoothing method of assigning weights to the motion contrast of nx×ny×nz voxels in the vicinity of a target pixel according to the difference between the weights of distance and the pixel value of the target pixel; and a smoothing method of outputting a value using a weight according to the similarity between motion contrast patterns of small areas around a target pixel and motion contrast patterns of small areas around peripheral pixels. A smoothing method while leaving blood flow information can be used.

At step S353, the image generating unit 147 acquires an initial value of a threshold (a display threshold) for determining a pixel to be displayed at step S355 and an initial value of a depth range of display from the display control unit 149. The initial value of the display range is normally set to about one fourth of the depth, in which substantially the surface layer of the retina is included. The whole depth range is not adopted as the initial value of the display range in order to increase the visibility of that main blood vessels and a capillary blood vessel network in the surface layer. In other words, if the surface layer including the main blood vessels and the capillary blood vessel network and a retinal pigment epithelium (RPE) layer including no blood vessel and having significant noise are displayed at the same time, it would be difficult to distinguish the main blood vessels and the capillary blood vessel network in the surface layer.

Figure 7A:
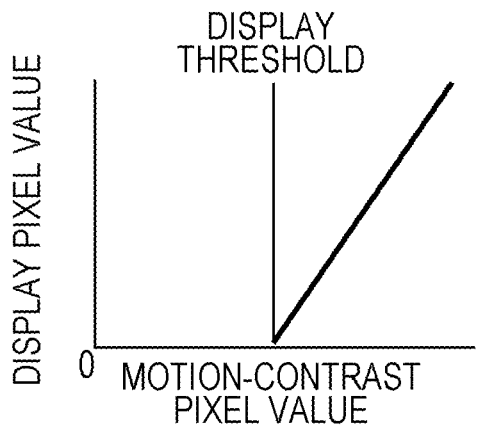
FIG. 7A is a diagram illustrating an example of a method for converting motion-contrast pixel values to display pixels according to an embodiment.
Figure 7B:
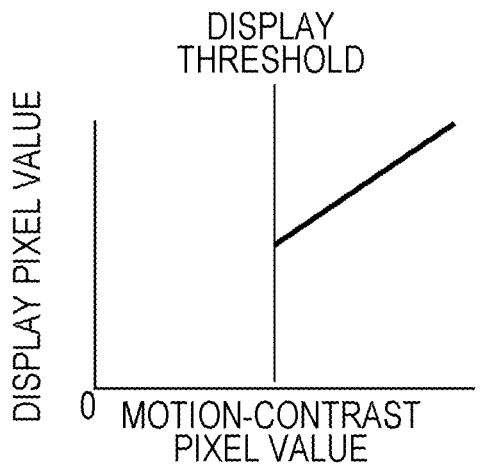
FIG. 7B is a diagram illustrating an example of a method for converting motion-contrast pixel values to display pixels according to an embodiment.

Next, at step S354, the image generating unit 147 performs display threshold processing for displaying pixels exceeding the initial value of the display threshold on the smoothed three-dimensional data. FIGS. 7A and 7B show examples of conversion from motion contrast (motion contrast pixel values) to display pixel values performed by this processing. FIG. 7A shows an example in which pixel values less than the display threshold is multiplied by 0, and pixels of the threshold to pixels of the maximum intensity are assigned display pixel values proportional thereto. FIG. 7B shows an example in which pixel values less than the display threshold is multiplied by 0, and the other pixel values are assigned display values multiplied by 1. In any case, motion contrast less than the display threshold is negated, and a region having motion contrast connected to display is separately displayed. In other words, the value of the motion contrast is controlled according to the result of comparison between the motion contrast and the threshold.

Figure 8B:
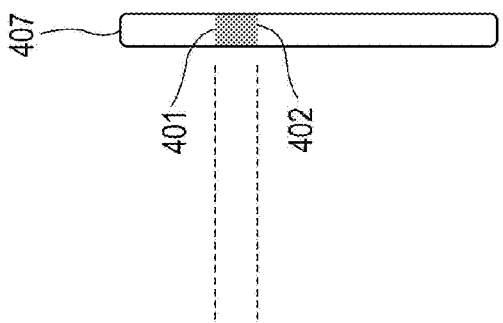
FIG. 8B is a diagram for illustrating an example of a GUI according to an embodiment.
Figure 8A:
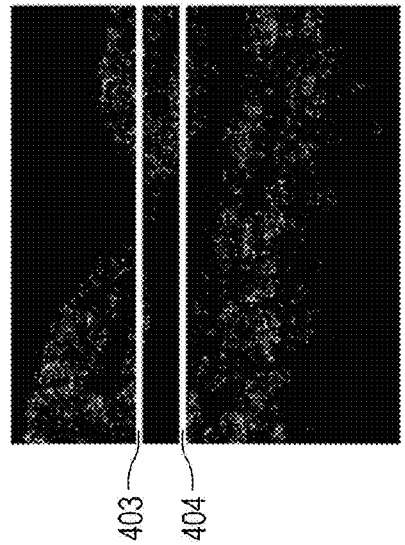
FIG. 8A is a diagram illustrating a tomographic image according to an embodiment.

At step S355, the display control unit 149 causes the motion contrast image subjected the threshold processing shown in FIG. 7A to be displayed on the display unit 146. For example, the display control unit 149 is designed to display the graphical user interfaces (GUIs) and the three-dimensional motion contrast image illustrated in FIG. 8B on the display unit 146 at the display step S355. In FIG. 8B, an area 400 is a display area frame provided in the display unit 146 for displaying the calculated three-dimensional motion contrast image. A slider 407, for adjusting the depth range in which the three-dimensional motion contrast image is to be displayed, is displayed on one side of the area 400. The technician performing an eye examination can designate the depth range of the three-dimensional motion contrast image to be displayed on the display unit 149 by dragging operating portion ends 401 and 402 of the slider 407 with a pointing device, such as a touchscreen or mouse. The examiner can change the display position in the depth direction without changing the width of the display range in the depth direction by dragging, for example, the center of the operating portion of the slider 407. FIG. 8A illustrates a tomographic image (a motion-contrast tomographic image) in the three-dimensional motion contrast image for the purpose of illustrating the corresponding depth. Bright lines 403 and 404 in the tomographic image indicate positions on the tomographic image corresponding to the operating portion ends 401 and 402 of the slider 407. In the display step S355, only a motion contrast image in an area 405 between the bright lines 403 and 404 in the display area frame 400. For example, the display control unit 149 may display either the images illustrated in FIGS. 8A and 8B or only the image illustrated in FIG. 8B on the display unit 149.

Another slider 406 is disposed below the display area frame 400 to adjust the threshold for determining pixels to be displayed. When the examiner drags the slider 406 with, for example, a mouse, the display threshold is changed at step S356 in FIG. 6, and the process returns to step S354 to update the three-dimensional motion contrast image to be displayed.

In this case, if the threshold can be changed to a value relative to the initial value, the equivalent effect can be obtained also for data on different subject eyes or parts. The above configuration allows the examiner to freely change the display depth range, allowing the most suitable display threshold to be set on the selected depth range. Likewise, when the examiner drags the slider operating portion ends 401 and 402 with a mouse to change the display range in the depth direction, the display range of the three-dimensional motion contrast image is changed at step S357. Then the process is returned to step S354 to update the three-dimensional motion contrast image to be displayed. In other words, the motion contrast image to be displayed is updated according to the change in display range.

Although the tomographic image illustrated in FIG. 8A is used only for illustration purpose, the tomographic image may be displayed in the display step. This allows the examiner to easily set the depth range for display. The tomographic image may be disposed by the side of the display area frame 400. A position corresponding to the tomographic image to be displayed may be displayed on the three-dimensional motion contrast image. For example, the display control unit 149 may display a line corresponding to the tomographic image on the three-dimensional motion contrast image.

The GUIs displayed on the display unit 146 are not limited to the form illustrated in FIGS. 8A and 8B. For example, the display control unit 149 may display the GUI illustrated in FIGS. 10A to 10C on the display unit 146. The elements illustrated in FIGS. 10A to 10C will be described with reference to FIG. 9A.

A slider 3001 receives the designation of the upper end of the depth range of the retina (an end adjacent to the vitreum) for generating a luminous en-face image 3005 and a motion-contrast en-face image. In other words, the slider 3001 corresponds to one example of a first slider for determining the upper end of the region in the depth direction. The display control unit 149 may control the slider 3001 so that the slider 3001 does not move to below a slider 3002. Controlling the slider 3001 prevents a boundary designated by the slider 3001 from being deeper than a boundary designated by the slider 3002.

The slider 3002 receives a designation of the lower end of depth range of the retina in the depth direction (an end adjacent to the choroid) for generating the luminous en-face image 3005 and a motion-contrast en-face image 3006. In other words, the slider 3002 corresponds to one example of a second slider for determining the lower end of the region in the depth direction. The examiner changes the range in the depth direction by dragging the sliders 3001 and 3002 with a mouse. The sliders 3001 and 3002 can be moved with a pointing device other than the mouse. For example, a touch panel does not need the mouse. It is needless to say that the sliders 3001 and 3002 can be moved by operations other than dragging.

For example, the image generating unit 147 acquires the positions and the amounts of movement of the sliders 3001 and 3002. An area next to the sliders 3001 and 3002 displays the names of a plurality of layers included in the eye fundus Er of the subject eye 118 in the order of depth. In other words, the display control unit 149 causes the display unit 146 to display the names of the plurality of layers in the subject eye 118 in the order of depth and also the sliders 3001 and 3002, which are movable in the direction in which the names of the plurality of layers are arranged, in an area by the side of the area in which the names of the plurality of layers are arranged. More specifically, the sliders 3001 and 3002 are displayed in an area next to the area of the display unit 146 in which the names of the plurality of layers are arranged. The names of the displayed layers are not limited to the examples in FIG. 9A. Other names may be displayed.

Figure 15:
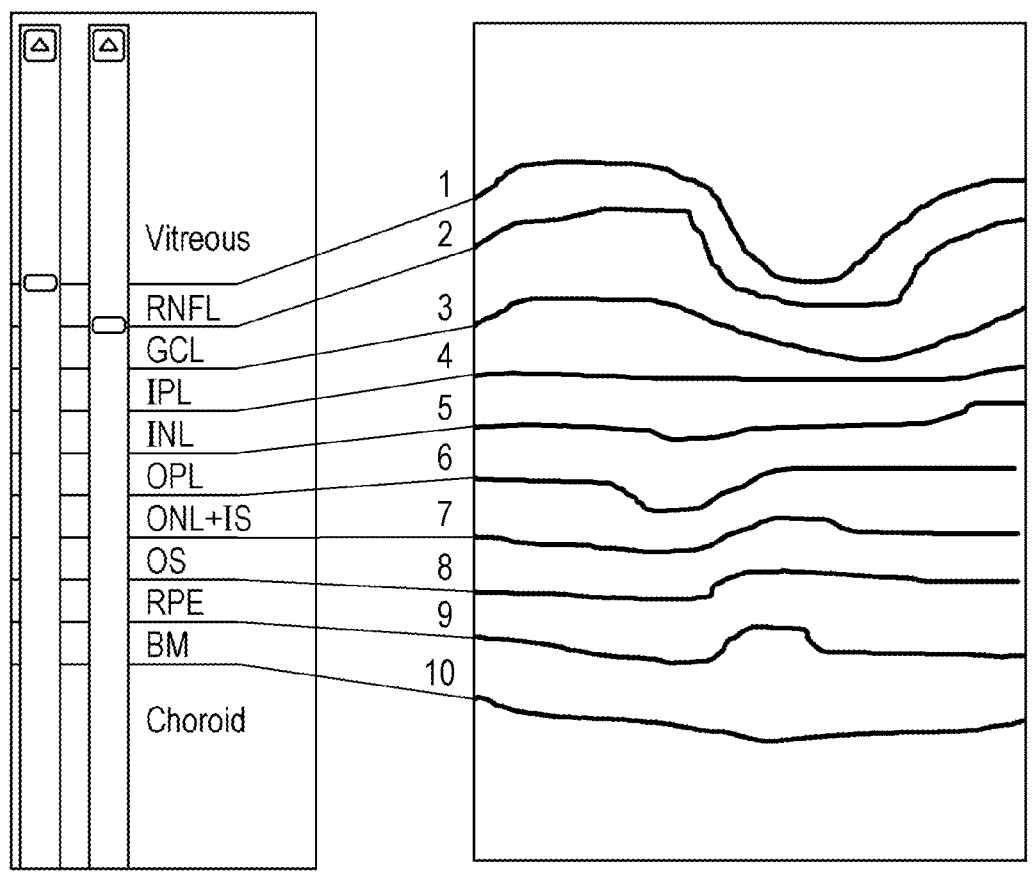
FIG. 15 is a diagram illustrating an example of a GUI according to an embodiment.

The display control unit 149 further displays a plurality of lines, on the display unit 146, that indicate layer boundaries and segment the area in which the plurality of layers are displayed at equal intervals by the names of the layers. The lines are associated with the layer boundaries acquired by segmentation, as shown in FIG. 15, and are equally spaced. In other words, the lines that segment the names of the layers are individually associated with the positions of the layer boundaries of the tomographic image. For example, when the slider 3001 is aligned with the line between Vitreous and RNFL, as in FIG. 9A, the image generating unit 147 determines that the boundary between Vitreous and RNFL is selected. When the slider 3002 is aligned with the line between INL and OPL, as in FIG. 9A, the image generating unit 147 determines that the boundary between INL and OPL is selected. In other words, when the sliders 3001 and 3002 are aligned with any lines of the plurality of lines, the image generating unit 147 determines that layer boundaries corresponding to the names of the layers are selected and generates an en-face image.

When a slider 3001' is positioned between the line between Vitreous and RNFL and the line between RNFL and GCL, as in FIG. 9B, the image generating unit 147 determines that a position in RNFL is selected. In other words, the use of the sliders 3001 and 3002 allows not only layer boundaries based on the result of segmentation but also any position between a layer boundary and a layer boundary, that is, any position in a layer, to be continuously selected. FIG. 9B illustrates an example of a GUI in which a depth range different from that in FIG. 9A is selected using sliders 3001' and 3002'. Reference signs 3001 to 3006 respectively correspond to reference signs 3001' to 3006'.

In FIG. 9A, the word "Synchronize" and a checkbox are displayed above the slider 3001. When the checkbox is selected by clicking or the like, the movements of the slider 3001 and the slider 3002 are synchronized with each other. In other words, the slider 3001 and the slider 3002 move while keeping the distance therebetween. A slider above the checkbox is used for switching between a luminance tomographic image 3003 and a motion-contrast tomographic image 3004. FIG. 9A shows that a 287th tomographic image is displayed.

The luminance tomographic image 3003 is a tomographic image at any given position in the three-dimensional tomographic image. The luminance tomographic image 3003 is, for example, a tomographic image on line A on the luminance en-face image 3005. The boundaries designated by the sliders 3001 and 3002 are superposed on the luminance tomographic image 3003. When the sliders 3001 and 3002 designate layer boundaries, the result of segmentation is displayed on the luminance tomographic image 3003. In other words, the display control unit 149 causes the display unit 146 to display a tomographic image of the subject eye 118 on which the boundaries in the depth direction that define regions in the depth direction are superposed.

The motion-contrast tomographic image 3004 is a tomographic image at any given position in the three-dimensional motion contrast image. An example of the motion-contrast tomographic image 3004 is a tomographic image on line A' on the motion-contrast en-face image 3006. When the sliders 3001 and 3002 designate layer boundaries, the result of segmentation is displayed on the luminance tomographic image 3003. In other words, the display control unit 149 causes the display unit 146 to display a tomographic image of the subject eye 118 on which the boundaries in the depth direction that define regions in the depth direction are superposed.

The boundaries displayed on the luminance tomographic image 3003 and the motion-contrast tomographic image 3004 are continuously moved as the sliders 3001 and 3002 move continuously. In other words, the sliders 3001 and 3002 receive designations to move the displayed boundaries in the depth direction. The way the boundaries move will be described later.

The luminance en-face image 3005 is an en-face image acquired from the depth range of the three-dimensional tomographic image designated by the sliders 3001 and 3002. The luminance en-face image 3005 is generated by the image generating unit 147. In other words, the image generating unit 147 generates the en-face image on the basis of the region in the depth direction determined according to the positions of the sliders 3001 and 3002. The use of the result of segmentation acquired by the detecting unit 148 allows the image generating unit 147 to generate an en-face image of any layer.

The motion-contrast en-face image 3006 is an en-face image acquired from the depth range of the three-dimensional motion contrast image designated by the sliders 3001 and 3002. The motion-contrast en-face image 3005 is generated by the image generating unit 147. In other words, the image generating unit 147 generates the en-face image on the basis of the region in the depth direction determined according to the positions of the sliders 3001 and 3002. In this embodiment, a plurality of motion-contrast en-face images are arranged to have the same size as the size of the luminance en-face image 3005. A conceivable method for arranging the plurality of motion-contrast en-face images is a method of determination based on the continuity of blood vessels (blood flow regions).

Figure 10B:
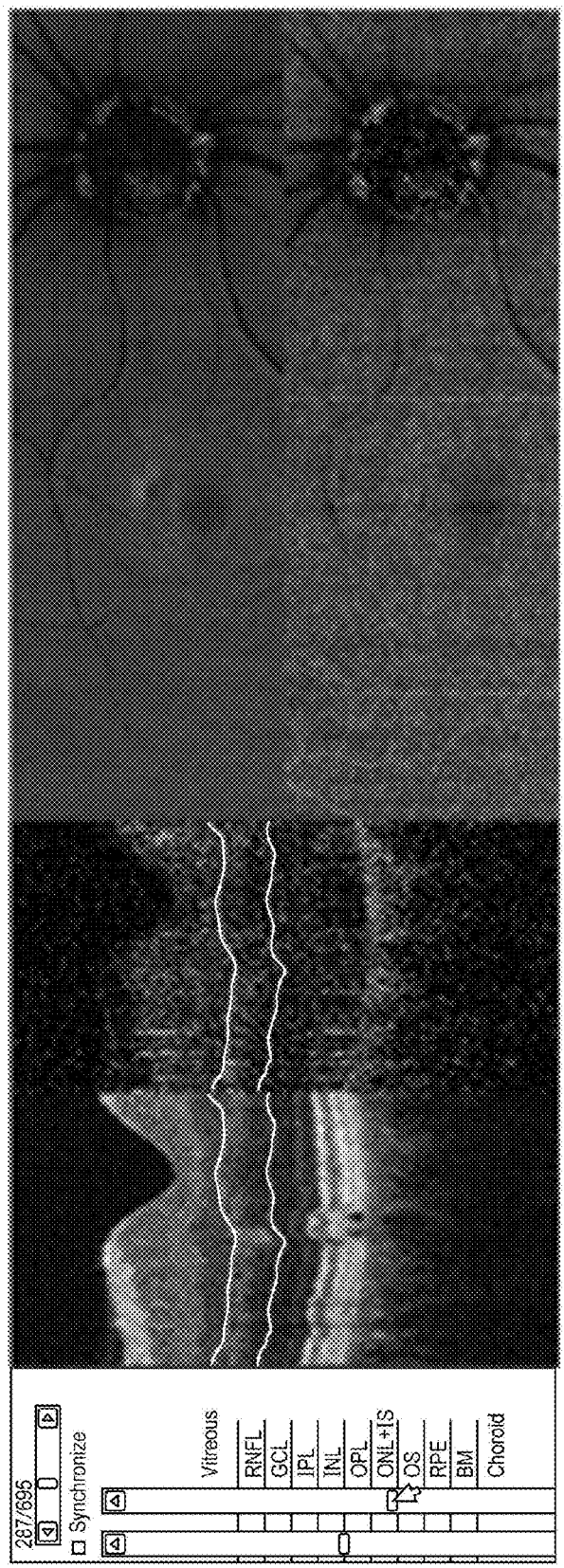
FIG. 10B is a diagram illustrating an example of a GUI according to an embodiment.
Figure 10C:
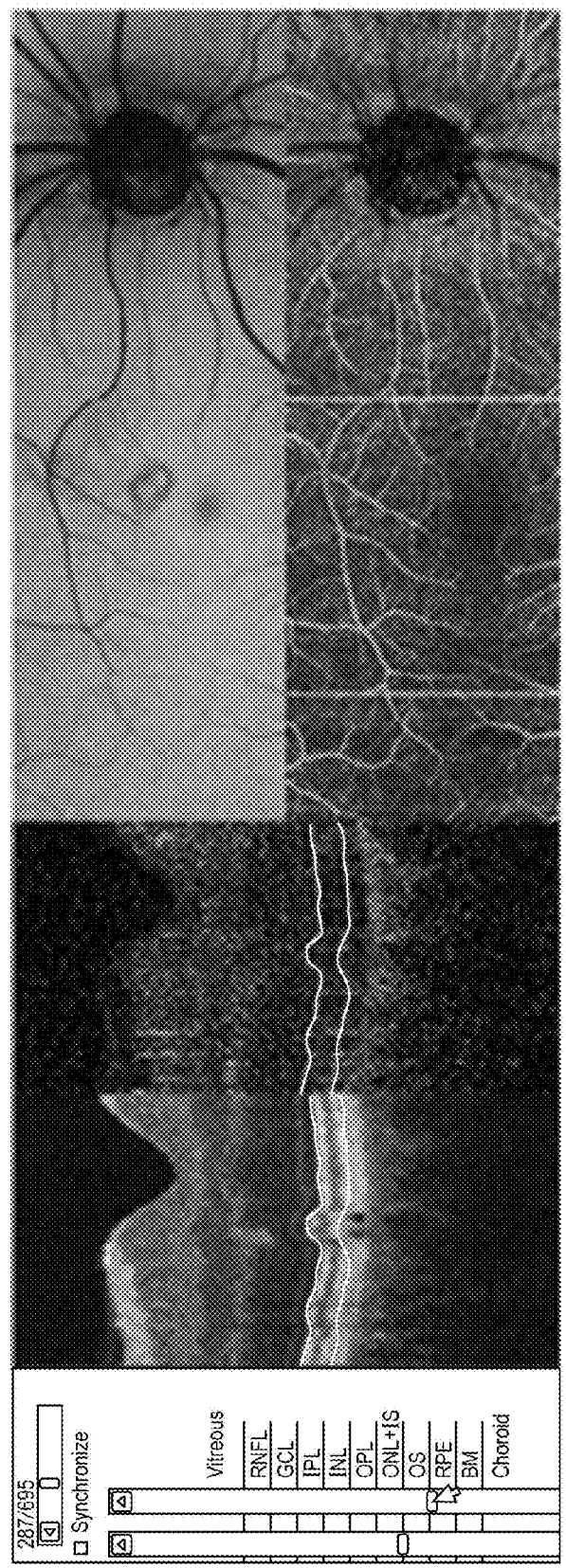
FIG. 10C is a diagram illustrating an example of a GUI according to an embodiment.

The luminance en-face image 3005 and the motion-contrast en-face image 3006 are updated by the image generating unit 147 and the display control unit 149 every time the sliders 3001 and 3002 are moved. In other words, when the sliders 3001 and 3002 are moved, it is determined to be Yes at step S357 in FIG. 6, and at step S355 the image generating unit 147 generates a new en-face image in the designated depth range. Then, the display control unit 149 displays the en-face image generated by the image generating unit 147 on the display unit 146. When the GUI illustrated in FIGS. 10A to 10C is used, the process at step S356 may be omitted.

The luminance en-face image 3005 and the motion-contrast en-face image 3006 are en-face images at substantially the same position of the eye fundus. The luminance tomographic image 3003 and the motion-contrast tomographic image 3004 are tomographic images at substantially the same position of the eye fundus.

An operation using the above GUI will be described. A case in which any layer boundary is designated using the slider 3001, and any position in any layer is designated using the slider 3002 will be described with reference to FIG. 16.

Figure 16:
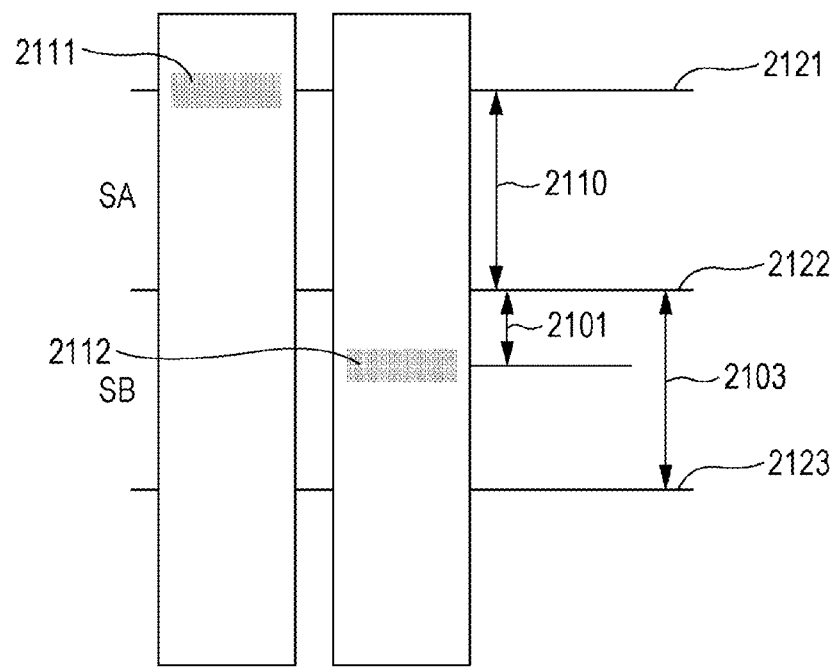
FIG. 16 is a diagram illustrating an example of a GUI according to an embodiment.

In FIG. 16, a slider 2111 for selecting the upper end of a depth range and a slider 2112 for selecting the lower end of the range respectively correspond to the sliders 3001 and 3002 in FIG. 9A. Layer boundaries 2121, 2122, and 2123 are based on the result of segmentation. The layer between the boundary 2121 and the boundary 2122 is referred to as a layer SA, and the layer between the boundary 2122 and the boundary 2123 is referred to as a layer SB. Layers selected using the sliders 2111 and 2112 are respectively the layer SA and the layer SB. The lower end of a depth range selected using the slider 2112 is positioned in the layer SB. When the slider 2122 is positioned in the layer SB like this, the image generating unit 147 determines what position in the layer SB is designated by the slider 2122. The entire width of the layer SB is denoted as a width 2103, and the width between the designated position and the layer boundary 2122 is denoted as a width 2101. Assuming that the width 2103 is 10, and the width 2101 is 3, a position corresponding to 30% of the entire layer SB from the layer boundary 2122 is the lower end of the depth range. Therefore, the depth range selected in FIG. 16 is the sum of a width 2110, which is the width of the entire layer SA, and the width 2101, which is the width of 30% of the layer SB.

Figure 17:
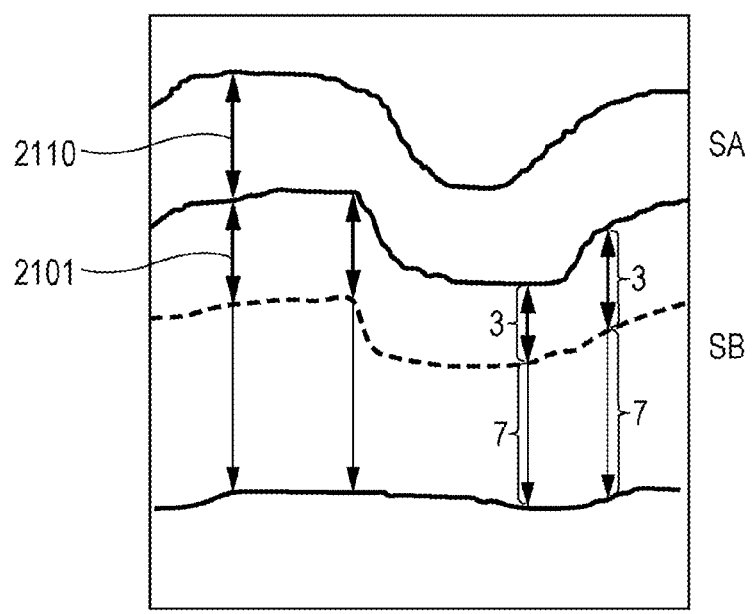
FIG. 17 is a diagram illustrating an example of a GUI according to an embodiment.

FIG. 17 illustrates the depth range selected in FIG. 16 on a tomographic image. In other words, FIG. 17 illustrates boundaries displayed on a luminance or motion-contrast tomographic image when the sliders 2111 and 2112 are set as in FIG. 16. A boundary corresponding to the slider 2112 is indicated by the dotted line. Since the position corresponding to 30% of the entire layer SB from the layer boundary 2122 is designated by the slider 2112, the ratio of the distance from the dotted line indicating the boundary to the layer boundary between the layer SA and the layer SB to the distance between the dotted line indicating the boundary and the layer boundary at the lower end of the layer SB is 3 to 7 at all positions perpendicular to the depth direction. For example, when the slider 2112 is moved downward to designate a position corresponding to 40% of the entire layer SB from the layer boundary 2122, the above ratio becomes 4 to 6. Therefore, the larger the width of the layer in which the dotted line is positioned, the larger the amount of movement of the dotted line in FIG. 17, even if the amount of movement of the slider 2112 is the same. The display control unit 149 increases the amount of movement of the boundary displayed on the display unit 146 relative to the amount of movement of the slider 2112 with an increasing layer thickness. In other words, if the layer thickness differs at different positions on the dotted line, the amount of movement of the dotted line differs even if the amount of movement of the slider 2112 is the same. In other words, the amount of movement of the boundary relative to the amount of movement of the slider 2112 depends on the layer thickness. In other words, when the slider 2112 receives a designation to move the boundary, the display control unit 149 moves the boundary by a different amount according to the thickness of the layer in which the boundary displayed on the display unit 146 is positioned. More specifically, when the slider 2112 receives a designation to move the boundary, the display control unit 149 moves points on the boundary perpendicular to the depth direction displayed on the display unit 146 by different amounts according to the difference in layer thickness at the positions in the direction perpendicular to the depth direction. In other words, the display control unit 149 corresponds to an example of a deforming means that changes the shape of the boundary that defines a region in the depth direction in the tomographic image of the subject eye 118 according to the thickness of the layer in which the boundary is positioned. The display control unit 149 also corresponds to an example of a determination means for determining the shape of a boundary that defines a region in the depth direction in the tomographic image of the subject eye 118 according to the thickness of the layer in which the boundary is positioned.

Since the display indicating the boundary is moved in this way, the shape of the display indicating the boundary, which is the shape of the layer boundary between the layer SA and the layer SB when the slider 2112 is positioned at the layer boundary 2122, changes gradually into a shape along the lower end of the layer SB. Thus, the display indicating the boundary can be smoothly changed.

FIGS. 10A to 10C illustrate an example of changes in the en-face images 3005 and 3006 and changes in boundaries superposed on the tomographic images 3003 and 3004 when the sliders 3001 and 3002 are synchronously moved.

Figure 14A:
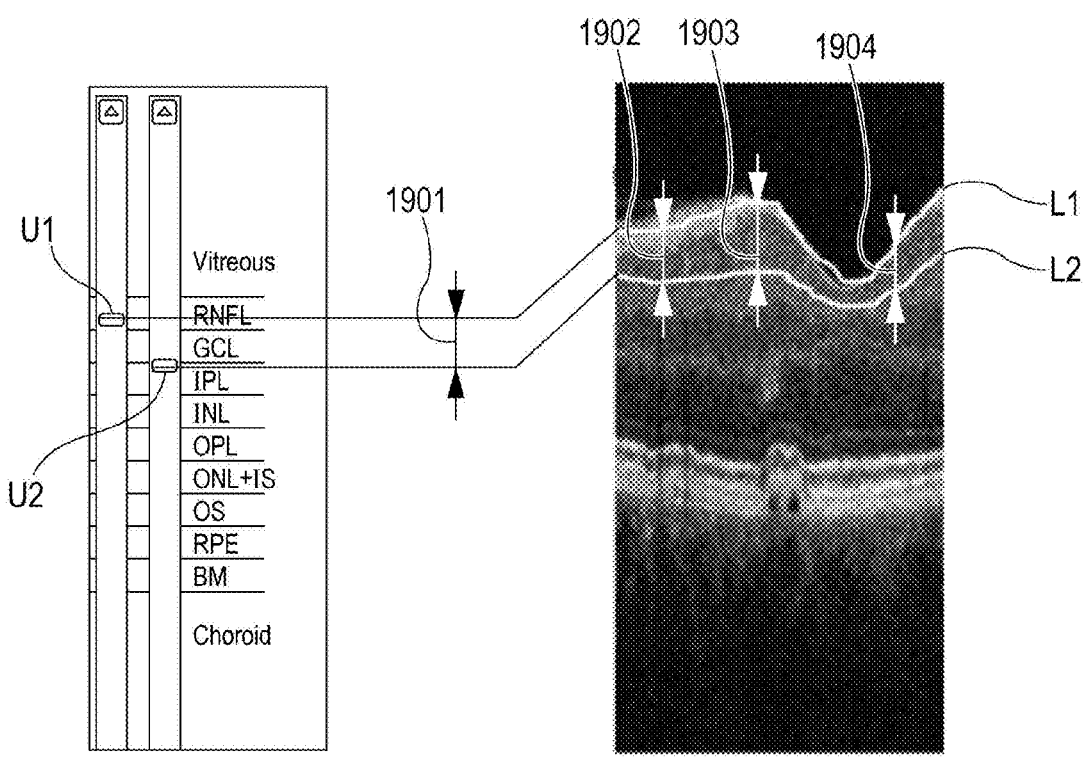
FIG. 14A is a diagram illustrating an example of a GUI according to an embodiment.
Figure 14B:
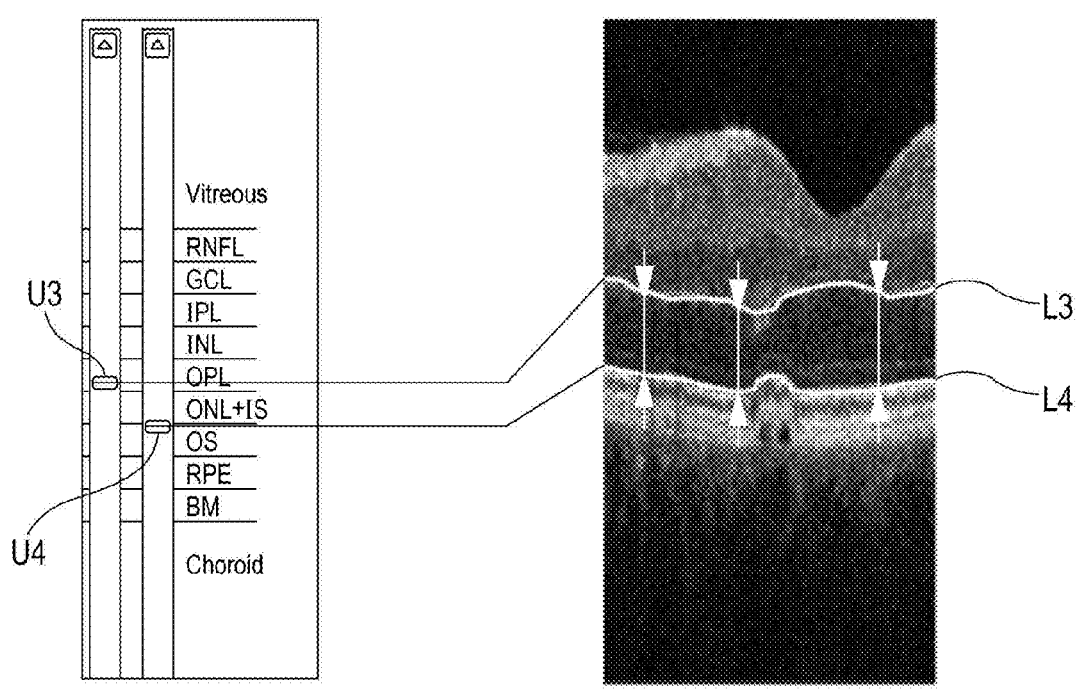
FIG. 14B is a diagram illustrating an example of a GUI according to an embodiment.
Figure 14C:
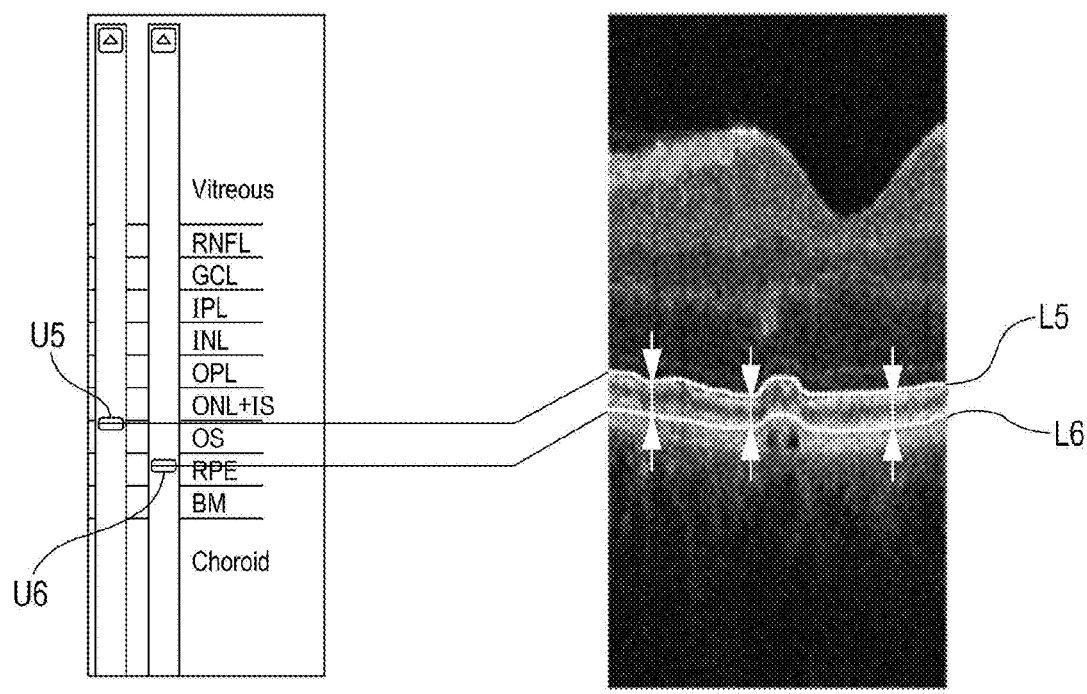
FIG. 14C is a diagram illustrating an example of a GUI according to an embodiment.

As shown in FIGS. 10A to 10C, by changing a depth range in which en-face images are to be generated using the sliders 3001 and 3002, the luminance en-face image 3005 and the motion-contrast en-face image 3006 are changed. The movement of the sliders 3001 and 3002 causes changes in the boundaries superposed on the tomographic images 3003 and 3004. The changes in boundaries will be described with reference to FIGS. 14A to 14C. FIGS. 14A to 14C illustrate the sliders and the tomographic image in FIGS. 10A to 10C. A slider U1 is a GUI for selecting the upper end of the depth range, and a slider U2 is a GUI for selecting the lower end of the depth range. The sliders U1 and U2 correspond to the sliders 3001 and 3002, respectively. A depth range for generating en-face images is determined according to the positions of the two sliders U1 and U2. Boundaries corresponding to the positions of the sliders U1 and U2 are respectively indicated as boundaries L1 and L2 in the tomographic image. The boundary L1 indicates the upper end of the depth range for generating en-face images, and the boundary L2 indicates the lower end of the depth range for generating the en-face images. Since the amounts of movement of the boundaries relative to the amount of movements of sliders differ according to the layer thickness, as described above, the width between the boundaries L1 and L2 in the vertical direction is not constant according to the position in the retina, as indicated by arrows 1902, 1903, and 1904 in FIGS. 14A to 14C.

FIG. 14B illustrates a display after the sliders U1 and U2 are moved from the state in FIG. 14A by dragging a mouse. The width between sliders U3 and U4 is the same as the width between the sliders U1 and U2 in FIG. 14A. However, the layer through which the two boundaries pass (layer thickness) changes as the sliders U1 and U2 move to the positions in FIG. 14B. Therefore, the width between boundaries L3 and L4 differs from the width between the boundaries L1 and L2 in FIG. 14A.

FIG. 14C illustrates a display after the sliders U3 and U4 are moved from the state in FIG. 14B by dragging the mouse. The width between sliders U5 and U6 is also the same as the width between the sliders U3 and U4 in FIG. 14B. However, the layer through which the two boundaries pass (layer thickness) changes as the sliders U3 and U4 move to the positions in FIG. 14C. Therefore, the width between boundaries L5 and L6 differs from the width between the boundaries L3 and L4 in FIG. 14B. For the same reason, the width between the boundaries L5 and L6 differ from the width between the boundaries L1 and L2 in FIG. 14A.

When boundary information based on the result of segmentation is not correct, the vitreum, which is the uppermost layer, and the choroid, which is the lowermost layer, may not selected using the sliders. Selection of the vitreum and the choroid may be made impossible by designating the moving range of the sliders as an absolute value. In this case, when the sliders reach the uppermost layer or the lower most layer, the movement by mouse dragging is stopped to prevent the display range in the depth direction from being changed.

The above embodiment facilitates designation of a region in the depth direction, such as a layer. Although a layer has generally been designated, the use of the GUI facilitates designation of not only layer boundaries but also any position in a layer.

In the above embodiment, the names of layers are displayed in the vicinity of the sliders. This facilitates determination of the depth range of the currently displayed en-face image.

Furthermore, the boundaries displayed on the tomographic image are not moved with the shape of the layer boundaries kept but are moved on the basis of the layer thickness. This allows the boundaries to smoothly align with other layer boundaries, making it easy to continuously move the boundaries.

Furthermore, since the en-face image is successively updated as the sliders move, the operator can move the sliders while viewing the en-face image.

In the above embodiment, two sliders are provided to designate the upper end and the lower end of the range. As an alternative, only one slider having a variable-shaped tab may be provided. The upper end of the range may be designated by dragging the upper end of the tab, and the lower end of the range may be designated by dragging the lower end of the tab.

The positions of the sliders and the names of the layers may be reversed left to right. The area in which the sliders are displayed and the area in which the names of the layers are displayed need not be adjacent to each other. It is only required that they are displayed side by side.

Second Embodiment

In designating a layer boundary, it is sometimes burdensome to correctly align a slider with a line indicating the layer boundary. In this case, the display control unit 149 may be configured to, when detecting clicking on the name of a retina layer displayed on the right of the slider, the display control unit 149 determines that a layer boundary corresponding to the name is selected.

For example, when "RNFL" is clicked in the example in FIG. 14A, the display control unit 149 moves the boundary L1 to the boundary between RNFL and GCL. Furthermore, the display control unit 149 moves the slider U1 to the position of a line between RNFL and GCL. When "RNFL" is clicked, the display control unit 149 may move the boundary L1 to the boundary between Vitreous and RNFL. In other words, designation of a layer boundary at the upper end of the designated layer and a layer boundary at the lower end when a layer name is clicked can be changed according to the setting.

Figure 13:
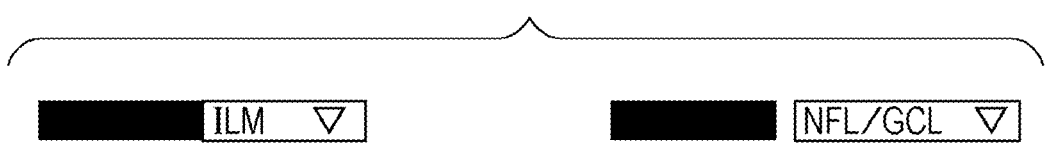
FIG. 13 is a diagram illustrating an example of a GUI according to an embodiment.

A pull-down menu that allows selection of a layer boundary, as shown in FIG. 13, may be displayed above the tomographic image 3003 or the like to enable a layer boundary to be selected from options. Also in this case, for example, when "RNFL" is selected, the display control unit 149 moves the boundary L1 to the boundary between RNFL and GCL. Furthermore, the display control unit 149 moves the slider U1 to the position of a line between RNFL and GCL.

The second embodiment allows a layer boundary to be easily designated also when a position in the depth direction is designated using a slider.

Third Embodiment

Figure 11A:
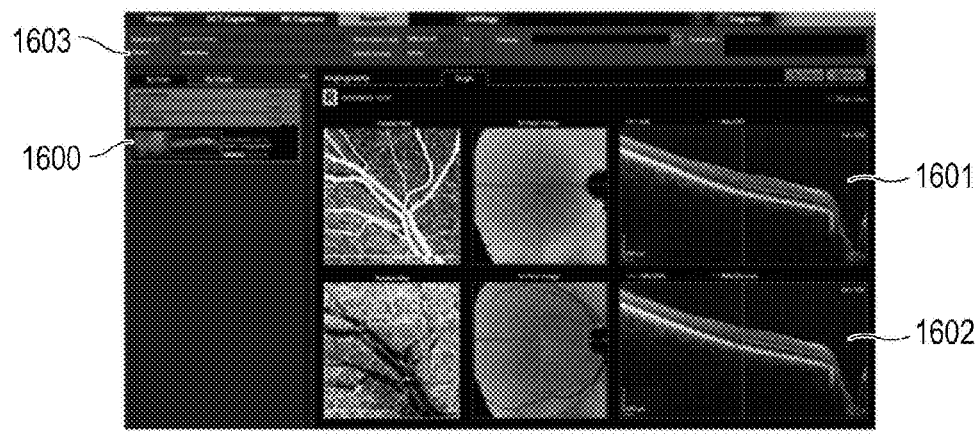
FIG. 11A is a diagram illustrating an example of a GUI according to an embodiment.

FIG. 11A illustrates an example of a report screen showing an examination result. The report screen shown in FIG. 11A is displayed on the display unit 146 under the control of the display control unit 149. The report screen displays a thumbnail 1600 of the examination, patient information 1603, and examination images 1601 and 1602. Each of the examination images 1601 and 1602 includes a motion-contrast en-face image, a luminance en-face image, and a luminance tomographic image from the left. The examination image 1601 and the examination image 1602 show the result of the same examination and differ in the depth range of the en-face images. For example, the depth range of the examination image 1601 is NFL, and the depth range of the examination image 1602 is RPE. In other words, the display control unit 149 can display en-face images in different depth ranges on the display unit 146 at the same time. Alternatively, the display control unit 149 may display en-face images in the same depth range, taken at different time, on the display unit 146.

In this case, it may be burdensome to select a depth range for each of the two examination images. In this case, it would be convenient to easily call up a selection range. For example, when display ranges in the depth direction are determined in advance for individual examinations, settings on the display ranges in the depth direction are stored in advance to easily call up the display ranges.

For example, display ranges in the depth direction are set, the settings are named and stored in a storage area, and the settings are called up using a pull-down menu.

Figure 11B:
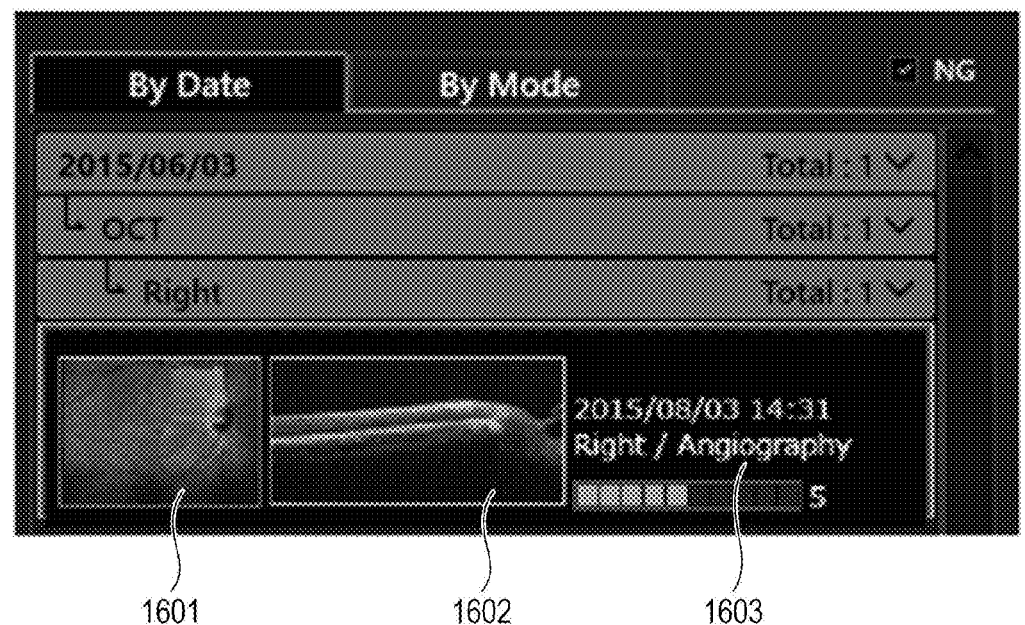
FIG. 11B is a diagram illustrating the detail screen of the GUI according to an embodiment.
Figure 12:
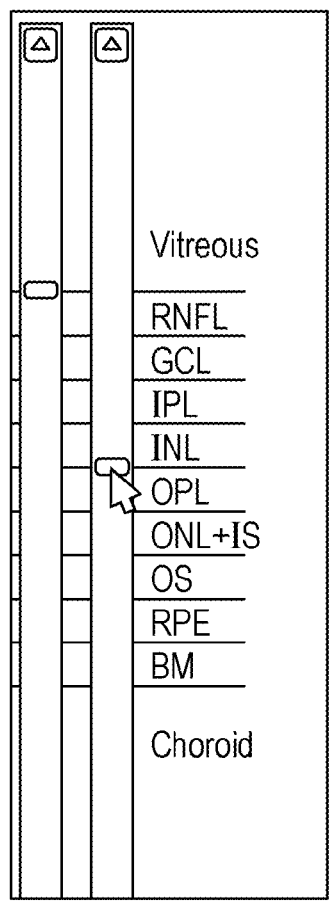
FIG. 12 is a diagram illustrating an example of a GUI according to an embodiment.

FIG. 11B illustrates the detail screen of the thumbnail 1600 in FIG. 11A. The examination image 1601 is a thumbnail of a SLO image, and the examination image 1602 is a thumbnail of a tomographic image. The examination information 1603 presents an imaging mode name "Angiography" indicating that the examination includes acquiring a motion-contrast en-face image. This allows the operator to easily find out that the examination includes acquiring a motion contrast image.

Although the examination image 1602 in FIG. 11B is a thumbnail of a tomographic image, a motion-contrast tomographic image may be displayed instead of the thumbnail of the tomographic image, or an SLO image, a tomographic image, or a motion-contrast tomographic image may be displayed on the thumbnail. In another alternative, a motion-contrast tomographic image and a motion-contrast en-face image may be displayed. When a motion-contrast en-face image is to be acquired by the examination, the display control unit 149 displays a thumbnail of a SLO image on the display unit 146. When a motion-contrast en-face image is to be acquired by the examination, a thumbnail of a motion-contrast en-face image may be displayed on the display unit 146 instead of the thumbnail of a SLO image.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™), a flash memory device, a memory card, and the like.

While the present invention has been described with reference to exemplary embodiments, it is to be understood that the disclosed exemplary embodiments are not limiting. The scope of the following claims is to be accorded the broadest interpretation so as to encompass all such modifications and equivalent structures and functions.

This application claims the benefit of Japanese Patent Application No. 2015-175023, filed Sep. 4, 2015, which is hereby incorporated by reference herein in its entirety.

What is claimed is:

1. An ophthalmic apparatus comprising:
a deforming unit configured to deform a shape of a boundary that defines a region of a tomographic image of a subject eye by moving the boundary in a depth direction according to layer thickness;
a generation unit configured to generate an en-face image based on the region in the depth direction defined by the shape of the boundary deformed by the deforming unit; and
a display control unit configured to control a display unit to display the tomographic image and the boundary,
wherein the deforming unit increases an amount of movement of the boundary displayed on the display unit as the layer thickness increases.

2. The ophthalmic apparatus according to claim 1, further comprising a receiving unit configured to receive an instruction to move the boundary in the depth direction,
wherein the deforming unit deforms the shape of the boundary when the receiving unit receives the instruction.

3. The ophthalmic apparatus according to claim 2, wherein the display control unit is further configured to cause the display unit to display names of a plurality of layers in the subject eye in an order of depth and to display a slider, the slider being movable in a direction in which the names of the plurality of layers are arranged, in an area parallel to an area in which the names of the plurality of layers are arranged,
wherein the receiving unit receives an instruction to move the boundary in the depth direction via the slider.

4. The ophthalmic apparatus according to claim 1, wherein the boundary is a layer boundary of a fundus of the subject eye.

5. The ophthalmic apparatus according to claim 1, wherein the display control unit controls the display unit to display the tomographic image and the boundary so that the boundary is superimposed on the tomographic image.

6. An ophthalmic apparatus comprising:
a deforming unit configured to deform a boundary that defines a region of a tomographic image of a subject eye by moving the boundary in a depth direction according to a layer thickness;
a receiving unit configured to receive an instruction to move the boundary in a depth direction;
a generation unit configured to generate an en-face image based on the region in the depth direction defined by the boundary; and
a display control unit configured to cause a display unit to display names of a plurality of layers in the subject eye in an order of depth and to display a slider, the slider being movable in a direction in which the names of the plurality of layers are arranged, in an area parallel to an area in which the names of the plurality of layers are arranged,
wherein the receiving unit receives an instruction to move the boundary in the depth direction via the slider.

7. The ophthalmic apparatus according to claim 6, wherein the slider comprises a first slider for determining a position of an upper end of a region in the depth direction and a second slider for determining a position of a lower end of the region in the depth direction.

8. The ophthalmic apparatus according to claim 6, wherein the slider is displayed in an area on the display unit, the area being adjacent to the area in which the names of the plurality of layers are arranged.

9. The ophthalmic apparatus according to claim 6, wherein the display control unit causes the display unit to display a plurality of lines that segment the area in which the names of the plurality of layers are displayed for the individual names of the layers,
wherein, when the slider is aligned with any one of the plurality of lines, the generation unit generates the en-face image based on a layer boundary corresponding to the selected line indicating the name of the layer.

10. The ophthalmic apparatus according to claim 9, wherein the plurality of lines are equally spaced.

11. The ophthalmic apparatus according to claim 6, wherein the boundary is a layer boundary of a fundus of the subject eye.

12. The ophthalmic apparatus according to claim 6, wherein the deforming unit increases an amount of movement of the boundary displayed on the display unit in response to a user input as the layer thickness increases.

13. A method of generating an en-face image with an ophthalmic apparatus, comprising:
deforming a shape of a boundary that defines a region of a tomographic image of a subject eye by moving the boundary in a depth direction according to a layer thickness;
generating an en-face image based on the region in the depth direction defined by the shape of the boundary deformed by the deforming; and
displaying the tomographic image and the boundary on a display unit,
wherein the deforming increases an amount of movement of the boundary displayed on the display unit as the layer thickness increases.

14. A non-transitory computer-readable medium storing a program which when executed by a processor causes the processor to perform a method of generating an en-face image, comprising:
deforming a shape of a boundary that defines a region of a tomographic image of a subject eye by moving the boundary in a depth direction according to a layer thickness;
generating an en-face image based on the region in the depth direction defined by the shape of the boundary deformed by the deforming; and
displaying the tomographic image and the boundary on a display unit, wherein the deforming increases an amount of movement of the boundary displayed on the display unit as the layer thickness increases.

* * * * *

UNITED STATES PATENT AND TRADEMARK OFFICE
CERTIFICATE OF CORRECTION

| | | |
|---|---|---|
| PATENT NO. | : 10,022,047 B2 | Page 1 of 1 |
| APPLICATION NO. | : 15/253260 | |
| DATED | : July 17, 2018 | |
| INVENTOR(S) | : Krzysztof et al. | |

It is certified that error appears in the above-identified patent and that said Letters Patent is hereby corrected as shown below:

On the Title Page

Item (12) "Yamashita" should read -- Krzysztof, et al. --.

Item (72) Inventor is corrected to read:
-- Piotrowski Krzysztof, Wroclaw (PL);
Yutaka Yamashita, Shiroi (JP) --.

Signed and Sealed this
Fourteenth Day of April, 2020

Andrei Iancu
*Director of the United States Patent and Trademark Office*